(12) United States Patent
Barak et al.

(10) Patent No.: US 11,185,395 B2
(45) Date of Patent: Nov. 30, 2021

(54) SYSTEMS AND METHODS OF AUTOMATED IN-SITU PREPARATION FOR MOUNTING OF PREFABRICATED CUSTOM DENTAL PROSTHESIS

(71) Applicants: HADASIT MEDICAL RESEARCH SERVICES AND DEVELOPMENT LTD, Jerusalem (IL); ROBOTOO INNOVATION LTD, Caesarea (IL)

(72) Inventors: Uri Barak, Caesarea (IL); Eyal Tarazi, Caesarea (IL)

(73) Assignee: ROBOTOO INNOVATION LTD, Caesarea (IL)

(*) Notice: Subject to any disclaimer, the term of this patent is extended or adjusted under 35 U.S.C. 154(b) by 385 days.

(21) Appl. No.: 16/217,250

(22) Filed: Dec. 12, 2018

(65) Prior Publication Data
US 2019/0209274 A1 Jul. 11, 2019

Related U.S. Application Data

(63) Continuation-in-part of application No. PCT/IB2017/054016, filed on Jul. 3, 2017.

(30) Foreign Application Priority Data

Jul. 3, 2016 (GB) .................................... 1611583

(51) Int. Cl.
*A61B 34/30* (2016.01)
*A61C 13/00* (2006.01)
(Continued)

(52) U.S. Cl.
CPC .......... *A61C 13/0001* (2013.01); *A61B 34/20* (2016.02); *A61B 34/30* (2016.02);
(Continued)

(58) Field of Classification Search
CPC ... A61C 13/0004; A61C 13/0001; A61C 5/80; A61C 5/90; A61C 5/77; A61C 5/82;
(Continued)

(56) References Cited

U.S. PATENT DOCUMENTS 4,579,530 A  4/1986 McLaughlin
4,997,369 A * 3/1991 Shafir ................ G05B 19/4207
                                                     433/72
(Continued)

FOREIGN PATENT DOCUMENTS

WO   2011159503   12/2011
WO   2012010916    1/2012

*Primary Examiner* — Heidi M Eide
(74) *Attorney, Agent, or Firm* — Mark David Torche; Patwrite Law

(57) ABSTRACT

A system and method of automated formation of a preparation stub, based on an a priori created computational geometrical model, configured to conform to a prefabricated fixed dental prosthesis, is described. The system includes a digital imaging facility with an image acquiring device and a three-dimensional data digitizer, a modeling facility with an exterior surface design module and an interior surface design module, a fabrication facility operatively with a computer-aided manufacturing module, as well as an application facility including an ablation tool and in-situ preparation module; application facility preferably includes an intra-oral feedbacking appliance with a distance measurement probe for automated feedback-controlled formation of a preparation stub.

17 Claims, 9 Drawing Sheets

(51) Int. Cl.
*A61C 13/107* (2006.01)
*A61C 5/77* (2017.01)
*A61C 5/80* (2017.01)
*A61C 1/08* (2006.01)
*A61C 5/82* (2017.01)
*A61B 34/20* (2016.01)
*A61C 5/90* (2017.01)
*A61C 1/00* (2006.01)
*A61C 5/00* (2017.01)
*A61C 9/00* (2006.01)

(52) U.S. Cl.
CPC .......... *A61C 1/0015* (2013.01); *A61C 1/0046* (2013.01); *A61C 1/082* (2013.01); *A61C 1/084* (2013.01); *A61C 5/007* (2013.01); *A61C 5/77* (2017.02); *A61C 5/80* (2017.02); *A61C 5/82* (2017.02); *A61C 5/90* (2017.02); *A61C 9/0053* (2013.01); *A61C 13/0004* (2013.01)

(58) Field of Classification Search
CPC ..... A61C 5/007; A61C 1/0015; A61C 1/0046; A61C 1/082; A61C 1/084; A61C 9/0053; A61B 34/20; A61B 34/30
See application file for complete search history.

(56) References Cited

U.S. PATENT DOCUMENTS

| | | |
|---|---|---|
| 5,345,490 A | 9/1994 | Finnigan et al. |
| 6,737,607 B2 | 5/2004 | Nicholas et al. |
| 7,328,077 B2 | 2/2008 | Durbin et al. |
| 7,346,417 B2 | 3/2008 | Luth et al. |
| 8,954,181 B2 | 2/2015 | MacLeod et al. |
| 2005/0177266 A1* | 8/2005 | Kopelman ............... A61C 5/77 700/117 |
| 2005/0186533 A1* | 8/2005 | Cohen .................... A61G 15/14 433/98 |
| 2011/0008751 A1 | 1/2011 | Pettersson |
| 2011/0070554 A1 | 3/2011 | Kopelman et al. |
| 2012/0291284 A1* | 11/2012 | Warden ................... A61C 13/34 29/896.1 |
| 2015/0057675 A1* | 2/2015 | Akeel ..................... G16H 40/63 606/130 |
| 2015/0182299 A1 | 7/2015 | Gurel et al. |
| 2017/0319302 A1* | 11/2017 | Mozes .................... A61B 34/76 |
| 2019/0038367 A1* | 2/2019 | Ciriello ................... A61B 34/00 |

* cited by examiner

SYSTEMS AND METHODS OF AUTOMATED IN-SITU PREPARATION FOR MOUNTING OF PREFABRICATED CUSTOM DENTAL PROSTHESIS

CROSS-REFERENCE TO RELATED APPLICATIONS

The present application is a continuation-in-part of international patent application PCT/IB2017/054016, published as WO2018/007935, entitled SYSTEMS AND METHODS OF AUTOMATED IN-SITU PREPARATION FOR MOUNTING OF PREFABRICATED CUSTOM DENTAL PROSTHESIS, filed 3 Jul. 2017, which claims priority from GB 1611583.4 filed 3 Jul. 2016, the content of which is incorporated herein in its entirety by this reference.

TECHNICAL FIELD

In general, the present invention pertains to the art of dentistry. In particular, the invention relates to systems and methods as well as computer readable storage media of automated in-situ preparation for mounting of prefabricated custom fixed dental prosthesis.

BACKGROUND ART

State of the art routine of clinical treatments for ultimate mounting of fixed dental prosthesis, colloquially also known as dental crown/veneer/bridge, typically involves at least two treatment sessions with a dentist. In certain instances, during a pre-treatment session, an impression or digital scanning of the tooth exterior surface is obtained, for fabrication of a mock-up of the exterior surface of the dental prosthesis.

Then during the first treatment session the tooth is subjected to cutting so that a substantial portion of the enamel is removed to form the preparation stub, onto which the dental prosthesis is thereafter to be mounted. Subsequently, impression of exterior surface of the preparation stub is obtained for fabrication of the interior surface of the dental prosthesis.

Finally, still during the first treatment session, the patient is fitted with a temporary dental prosthesis that is fabricated at the clinic, as per the dental prosthesis mock-up using rapid polymeric hardening based techniques.

The exterior surface of the tooth impression as well as the exterior surface impression of the preparation stub, both obtained during the first treatment session, are then sent to a dental technician/lab for fabrication of custom exterior surface and interior surface of the dental prosthesis, respectively.

During the second treatment session, dentist first removes any previously mounted temporary dental prosthesis and then the custom dental prosthesis fabricated by the technician is finally mounted onto the preparation stub, typically by using specific cements and/or adhesives.

U.S. Pat. No. 7,328,077 teaches a method and system for automated mass manufacturing of custom tooth die models for use in the fabrication of dental prosthesis. Methods and systems for treating teeth according to U.S. Pat. No. 7,328,077 include capturing a digital dental model taken within an oral cavity; modifying the digital model in planning a dental treatment or in designing a tooth die model for a dental prosthesis; creating physical models from the original or modified digital models: and using the physical models as a pattern for fabrication and fit check of a dental prosthesis.

U.S. Pat. No. 8,954,181 teaches systems and methods for designing and manufacturing custom dental preparation guides. The dental computer-aided design (CAD) and/or computer-aided manufacturing (CAM) system in U.S. Pat. No. 8,954,181 forms a custom dental preparation guide for guiding a dental tool that alters and shapes a tooth structure to which a custom prosthetic dental item is to be attached. The system of U.S. Pat. No. 8,954,181 acquires an optical measurement and an x-ray of at least one dental structure and correlates the acquired optical measurement and the x-ray to form a model of the at least one dental structure. The system of U.S. Pat. No. 8,954,181 generates a model of a reduced tooth structure based on the model of the at least one dental structure and provides at least one dental preparation guide based on the model of the reduced tooth structure.

U.S. Pat. No. 5,345,490 teaches a method and apparatus for converting computed tomography (CT) data into finite element models. The system of U.S. Pat. No. 5,345,490 generates both 2-D and 3-D models using the automatic mesh generators, QUADTREE and OCTREE, which are founded on recursive spatial decomposition. Multiple slices of CT data in U.S. Pat. No. 5,345,490 are obtained by scanning the object to be modeled. The slices are stacked and processed according to U.S. Pat. No. 5,345,490 to form a discrete solid model. The discrete solid model in U.S. Pat. No. 5,345,490 is an alternate geometry defined discretely rather than with continuous analytic curves and surfaces but still provides a foundation for automatic mesh generation. Since the QUADTREE and OCTREE automatic mesh generators map naturally to the discrete solid model, the integration of CT technology and automatic mesh generation according to U.S. Pat. No. 5,345,490 can be achieved.

US20150182299 teaches an intraoral device for automated preparation of the teeth with a view to performing partial or peripheral dental restoration, which includes: a splint suitable for being positioned in the mouth of a patient, said splint including a means for maintaining the position thereof inside said mouth; at least one mobile cutting tool combined with said splint; and an electronic management unit which makes it possible to control said cutting tool, characterised in that: said cutting tool is configured so as to cut at least the labial surface of the tooth to be prepared, said tool being mounted on a mobile carriage moving along a rail attached to the splint, opposite the labial surface of the tooth to be prepared, said rail having a curvature that matches the dentition of the patient; said splint includes at least one 3D digitisation tool arranged such as to digitise at least the labial surface of said tooth to be prepared, said digitisation tool being connected to the management unit so that the digitised data can be transferred to said management unit; and said management unit is configured so as to control the movement of said cutting tool in accordance with the digitised data.

U.S. Pat. No. 7,346,417 teaches method and system which can be used in the fields of medicine and dentistry, as well as for the most varied types of material working in different areas of application and model working, provides that an exact removal of material or a highly precise, reproducible material working can be realized by acquiring, storing and processing data pertaining to position and/or orientation of an effector and their changes relative to the position of at least one reference body. The effector in U.S. Pat. No. 7,346,417 is controlled and/or regulated with regard to its power and/or parameterization based on a predetermined working volume, material volume removed and remaining material volume. A first marking support with markings is arranged in U.S. Pat. No. 7,346,417 on a handpiece with the effector, where the handpiece is connected to a control unit, and a second marking support with markings is attached to the material object or tissue object.

U.S. Pat. No. 4,579,530 teaches method of fabricating a porcelain veneer casing for use in the restoration of damaged teeth in which a porcelain layer is built up on a model of the teeth. The model is removed by erosion caused by the blast of air under pressure containing glass balls. U.S. Pat. No. 4,579,530 also includes the method of restoration of damaged teeth using the aforesaid porcelain veneer casing and the porcelain veneer casing as an article of manufacture.

WO2011159503 teaches a method of making a multi-chromatic dental appliance, where a first article can be formed of a first material based on a first digital surface representation having a desired outer shape of the dental appliance. A portion of the first article in WO2011159503 can then be removed to form an outer layer of the dental appliance comprising a cavity dimensioned to accommodate an inner layer. A second article in WO2011159503 can be formed by filling the cavity of the first article with a second material. The second material in WO2011159503 can have at least one different optical property than the first material.

WO2012010916 and US2013/0216972 to Kolozsvary that are considered a closest prior art teaches automation of process and apparatus for computer-controlled preparation of teeth, during said process preparing the tooth-stump(s) holding the prothetic piece as pillar(s), takes place on basis of a digital plan of three dimensions, with a combined laser head of small size, matching the size of the oral cavity, moving along a trajectory fixed to a frame of face-bow controlled by a computer, preparing teeth-stump(s) before placing into the mouth the prosthetic piece produced by CAD/CAM technique—bridge, crown, insert, etc. During the process of WO2012010916 the designing of the preparation of the dental stump(s) serving as pillar tooth/teeth for the fixing of the prothetic piece as Step 1 the dentist, the patient's mandible into maximum opening position with the help of the telescopic frame of maxillo-mandibular fixing, as step 2 on basis of the complete digital plan the computer directs the combined laser head in the car to the pillar tooth to be prepared, as step 3 the laser miller with mobility towards every direction of the space situated on the combined laser head directed to the proper spot, carries out the preparation of the pillar tooth on basis of the complete digital plan. The apparatus according to the invention is provided with control optics for surveying the preparation of tooth stump(s), which is made by a combined laser head containing a laser miller emitting hard laser beam. The supporting, fixing points of the telescopic frame of maxillo-mandibular fixing on the patient's maxilla-mandibular area comprising part of the automatic tooth stump preparing apparatus.

EXOCAD® software available from Exocad GmbH, at Julius-Reiber 37 Darmstadt 64293 Germany, provides a state-of-the-art framework with design capabilities of full contour modeling of functional dental prosthesis. EXOCAD® software includes multiple high-quality tooth libraries.

Yomi® available from Neocis Inc. at 2800 Biscayne Blvd Suite 600, Miami, Fla. 33137 provides dental surgeons with guidance through the of haptic robotic technology and multisensory feedback to help achieve the right location, angulation and depth to place dental implants exactly according to pre-devised plans.

DVA Die Spacer available from Dental Ventures of America, Inc. from 1787 Pomona Road, Suite C Corona, Calif. 92880 USA is a colored, paint-on material applied to dies that adds a desired dimension to the surface of the die to function as a "spacer." The extra thickness created by the Die Spacer results in additional space between the inners surface of the prosthetic and the outer surface of the preparation stub to accommodate the dental cement used for bonding the inners surface of the prosthetic to the outer surface of the preparation stub.

US20110008751 teaches a method and system useful for planning a dental restorative procedure of a patient and for producing at least one dental restoration or product related thereto to be used in said dental restorative procedure are disclosed. Input data from different sources, e.g. 3D data from a CT scan of a patient with a dental impression tray including a previously prepared dental impression of the patient in the patient's mouth, is matched with data from a high resolution 3D scan of the same dental impression.

Takafumi Otani et al. in THE JOURNAL OF PROSTHETIC DENTISTRY, as of 2015 August teach a study on *In vitro evaluation of accuracy and precision of automated robotic tooth preparation system for porcelain laminate veneers*, assessed an automated robotic tooth preparation system for porcelain laminate veneers (PLVs) for accuracy and precision compared with conventional freehand tooth preparation. Twenty maxillary central incisor tooth models were divided into two groups. Ten were assigned to a veneer preparation with a robotic arm according to preoperative preparation design-specific guidelines (experimental group). Ten were assigned to conventional tooth preparation by a clinician (control group). Initially, all tooth models were scanned with a 3-dimensional (3D) laser scanner, and a tooth preparation for PLVs was designed on a 3D image. For the experimental group, an electric high-speed handpiece with a 0.9-mm-diameter round diamond rotary cutting instrument was mounted on the robotic arm. The teeth were prepared automatically according to the designed image. For the control group, several diamond rotary cutting instruments were used to prepare the tooth models according to preoperative preparation design guidelines. All prepared tooth models were scanned. The preoperative preparation design image and scanned postoperative preparation images were superimposed. The dimensional difference between those two images was measured on the facial aspect, finish line, and incisal edge. Differences between the experimental and the control groups from the 3D design image were computed. Accuracy and precision were compared for all sites and separately for each tooth surface (facial, finish line, incisal).

U.S. Pat. No. 6,737,607 teaches an apparatus for cutting a workpiece. A laser beam according to U.S. Pat. No. 6,737,607 is directed at successive points along a workpiece surface to be cut and a sensor emits a sensing beam directed at the same successive points as the cutting beam. A beam combining device in U.S. Pat. No. 6,737,607 receives both the sensor beam and the cutting beam and causes downstream beam segments to be collinear with each other as they impinge the workpiece surface. The cutting is thereby according to U.S. Pat. No. 6,737,607 able to be carried out in a single pass, and is precise, repeatable and independent of cutting depth, angle of cutting, scoring patterns, material inconsistency, material color, and surface grain variability.

The iTero Element Intraoral Scanner, obtainable from Cadent, Inc. 640 Gotham Parkway Carlstadt N.J., 07072-2405 USA, referenced herein, employs parallel confocal imaging technology for scanning to achieve high precision and accuracy without powder or complicated hovering.

MicronTracker obtainable from Claron Technology, at Carlton St 120, Suite 217, Toronto M5A 4K2 Canada, is a real-time sub-millimeter optical pose-tracking products. MicronTracker products are fully passive, using available visible light to detect and track objects of interest. The objects are marked using small checkered target regions called Xpoints. MicronTracker cameras connect to the host PC using a standard IEEE-1394 (FireWire) interface. Multiple cameras may be simultaneously activated to create a larger field of measurement and/or reduce line-of-sight interruptions. MicronTracker 3 is fully developed, tested and certified including several models, Hx40, Hx60, Sx60 and H3-60, differentiated by the size of their field of measurement (FOM) and measurement rate.

US20110070554 teaches feedback data useful in prosthodontic procedures associated with the intra oral cavity is provided. In US20110070554 a 3D numerical model of the target zone in the intra oral cavity is provided and manipulated, so as to extract particular data that may be useful in a particular procedure, for example data relating to the finish line or to the shape and size of a preparation. The relationship between this data and the procedure in US20110070554 is then determined, for example the clearance between the preparation and the intended crown. Feedback data, according to US20110070554 indicative of this relationship, is then generated, for example whether the preparation geometry is adequate for the particular type of prosthesis.

In light of that robotic tooth preparation systems known in the art, they are implementable inter alia for in-situ tooth preparation, since the enablement of automated in-situ formation of a preparation stub based on a virtual computational CAD model with automated manufacture of a prefabricated custom dental prosthesis based on the virtual computational CAD model entails a clear clinical benefit.

In light of that robotic tooth preparation systems known in the art are implementable inter alia for in-situ tooth preparation, since the enablement of automated in-situ formation of a preparation stub based on a virtual computational CAD model with automated manufacture of a prefabricated custom dental prosthesis based on the virtual computational CAD model entails a clear clinical benefit, such combination of automated in-situ formation of the preparation stub with automated prefabrication of custom dental prosthesis based on the same virtual CAD model satisfies a long-felt need in the art.

SUMMARY OF THE INVENTION

There is provided in accordance with embodiments of the present invention a system for automated formation of a preparation stub, based on an a priori created computational geometrical model, configured to conform to a prefabricated fixed dental prosthesis, including a digital imaging facility, configured to generate a digitized three-dimensional imprint model of at least one subject tooth of a patient, for future mounting of the prefabricated fixed prosthesis thereon, including: an image acquiring device configured to obtain a plurality of images of the subject tooth and a three-dimensional data digitizer, operatively connected to the image acquiring device, the three-dimensional data digitizer is configured to receive raw data of the plurality of images of the subject tooth and process the raw data to generate the digitized three-dimensional imprint of the subject tooth; a modeling facility operatively connected to the digital imaging facility, configured to receive the digitized three-dimensional imprint model of the subject tooth, including: an exterior surface design module, configured for modelling an exterior surface of the prefabricated fixed prosthesis and generating a digital three-dimensional model of the exterior surface and an interior surface design module, configured for modelling and generating a respective digital three-dimensional model of an interior surface of the prefabricated fixed prosthesis and/or an exterior surface of the preparation stub; a fabrication facility operatively connected to the modeling facility and receiving the digital three-dimensional exterior and interior surface models of the prefabricated fixed prosthesis, including a computer-aided manufacturing (CAM) module, configured to process a workpiece according to the digital three-dimensional exterior and interior surface models and to manufacture the prefabricated fixed dental prosthesis; an application facility operatively connected to the modeling facility and receiving at least one of the digital three-dimensional models from the modeling facility, including: an ablation tool configured to controllably remove dental tissue from the subject tooth, so as to form the preparation stub and an automated in-situ preparation module configured positioning of the ablation tool according to a digital three-dimensional model of the interior surface of the prefabricated fixed prosthesis and/or the exterior surface of the preparation stub.

There is provided in accordance with embodiments of the present invention a system for automated feedback-controlled formation of a preparation stub, in which an application facility includes an intra-oral feedbacking appliance including a distance and/or position and/or orientation and/or angulation measurement mechanism, configured to determine a distance and/or position and/or orientation and/or angulation relatively of the ablation tool to an ablation site on the subject tooth and/or the magnitude of the force with which the ablation tool is engaged to the ablation site.

There is provided in accordance with embodiments of the present invention a system for automated feedback-controlled formation of a preparation stub, based on an a priori created computational geometrical model, configured to conform to a prefabricated fixed dental prosthesis, in which at least one parameter related to positioning of the ablation tool, actuation of the ablation tool and intensity of operation of the ablation tool, is determined according to the distance and/or position and/or orientation and/or angulation relatively of the ablation tool relative to an ablation site on the subject tooth obtained by an intra-oral feedbacking appliance. It should be noted that intra-oral feedbacking appliance itself is not necessarily intra-orally positioned but optionally extra-orally positioned, rather the distance and/or position and/or orientation and/or angulation measurement of the ablation tool relatively to an intra-oral ablation site on the subject tooth. In some embodiments, the tactile feedbacking may include a haptic mechanism configured to determine resistance, pressure and/or position, related to the ablation tool, so as to calculate the strength, delicacy and complexity in formation or at least in guidance/assistance to operator in formation of a preparation stub.

There is provided in accordance with embodiments of the present invention a system for automated feedback-controlled formation of a preparation stub, in which the intra-oral feedbacking appliance is configured to iteratively attain a plurality of distance measurements of an ablation site on the subject tooth and wherein the at least one parameter selected from the group consisting of: a parameter elated to the positioning of the ablation tool, a parameter related to actuation of the ablation tool and a parameter related intensity of operation of the ablation tool, is repeatedly re-determined according to the a plurality of distance measurements.

There is provided in accordance with embodiments of the present invention a system for automated feedback-controlled formation or at least guidance/assistance to operator in formation of a preparation stub, in which the tactile feedbacking appliance is configured to iteratively attain a plurality of haptic or other type of contact measurements of the contact between an ablation tool and an ablation site on the subject tooth wherein the at least one parameter selected from the group consisting of: a parameter related to the positioning of the ablation tool, a parameter related to actuation of the ablation tool and a parameter related intensity of operation of the ablation tool, is repeatedly re-determined according to the a plurality of distance measurements.

There is provided in accordance with embodiments of the present invention a method for automated formation of a preparation stub including: obtaining a plurality of images of at least one subject tooth of a patient, for future mounting of the prefabricated fixed prosthesis thereon; processing raw data of the plurality of images of the subject tooth and generating a digitized three-dimensional imprint model of the subject tooth; transmitting the digitized three-dimensional imprint model of the subject tooth to the modeling facility; modelling an exterior surface of the prefabricated fixed prosthesis and generating a digital three-dimensional model of the exterior surface; modelling and generating a respective digital three-dimensional model of at least one surface selected from the group consisting of: an interior surface of the prefabricated fixed prosthesis and an exterior surface of the preparation stub configured to conform to the prefabricated fixed dental prosthesis; processing a workpiece according to the digital three-dimensional exterior and interior surface models to manufacture the prefabricated fixed dental prosthesis; transmitting a digital three-dimensional model of at least one surface selected from the group consisting of: an interior surface of the prefabricated fixed prosthesis and an exterior surface of the preparation stub, to a controller of an automated in-situ preparation module; devising an operational plan for the automated in-situ preparation module and commanding the automated in-situ preparation module to controllably remove a portion of dental tissue from the subject tooth.

There is provided in accordance with embodiments of the present invention a method for automated feedback-controlled formation of a preparation stub including: performing at least one feedbacking in-situ measurement of an ablation site on the subject tooth; comparing results of the at least one feedbacking in-situ measurement of the ablation site on the subject tooth to a digital three-dimensional model of at least one surface selected from the group consisting of: an interior surface of the prefabricated fixed prosthesis and an exterior surface of the preparation stub; determining whether differences determined at the step of comparing exceed a predetermined threshold; devising an updated operational plan for the automated in-situ preparation module and commanding the automated in-situ preparation module to controllably remove yet another portion of the dental tissue from the subject tooth, if the differences determined at the step of comparing are found to exceed the predetermined threshold at the step of determining.

There is provided in accordance with embodiments of the present invention a method for automated feedback-controlled formation of a preparation stub including iteratively performing a plurality of distance measurements of the ablation site on the subject tooth and repeatedly performing the steps comparing, determining and devising the updated operational plan.

There is provided in accordance with embodiments of the present invention a method for automated feedback-controlled formation of a preparation stub including performing primary in-situ scanning of the subject tooth.

DEFINITIONS

The term QUADTREE, as referred to herein, is to be construed as any tree data structure in which each internal node has exactly four children. QUADTREEs are most often used to partition a two-dimensional space by recursively subdividing it into four quadrants or regions. The regions may be square or rectangular, or may have arbitrary shapes.

The term OCTREE, as referred to herein, is to be construed as any tree data structure in which each internal node has exactly eight children. OCTREEs are most often used to partition a three-dimensional space by recursively subdividing it into eight octants. OCTREEs are the three-dimensional analog of QUADTREEs.

The terms robot-assisted surgery and/or computer-assisted surgery or alike, as referred to herein, is to be construed as any clinical appliance that uses either autonomous, guided, assisted or other robotic systems to aid in clinical procedures and allows the surgeon to have the normal movements associated with the clinical treatment performed whilst the robotic arms carry out and/or at least guide/assist the surgeon in carrying out those movements using end-effectors and manipulators to perform the actual actions on the patient. In computer-controlled systems the clinician uses a computer to control the robotic arms and its end-effectors, though these systems can also still use telemanipulators for their input.

The term fixed dental prosthesis, as referred to herein, is to be construed in accordance with the definition of this term as set forth in THE GLOSSARY OF PROSTHODONTIC TERMS, (Annex 3), namely as any dental prosthesis that is luted, screwed or mechanically attached or securely retained to natural teeth, tooth roots, and/or dental implant abutments that furnish the primary support for the dental prosthesis. This may include replacement of one to sixteen teeth in each dental arch. If a metallic or ceramic component is included within the fixed dental prosthesis, that component is termed the framework. Dental prostheses (fixed dental prostheses, re-movable dental prostheses) as well as maxillofacial prostheses can be supported and retained in part or whole by dental implants. Terminology to assist in describing the means of retention, support and dental materials should be limited to concatenation of three and no more than four adjectives to provide clarity. Descriptive terminology (modifiers) expressed as adjectives to each fixed dental prosthesis may include such items as the method of retention, composition, nature of support, design characteristics, and/or form of anchorage.

The term automatic mesh generation is an algorithmic procedure which produces a valid finite element mesh in a domain of arbitrary complexity, given no inputs besides the geometric description of the part and some element discretization information.

The term automated in-situ preparation for mounting of prefabricated custom dental prosthesis, as referred to herein, is to be construed as including inter alia at least guidance and/or assistance to operator in preparation for mounting of prefabricated custom dental prosthesis.

It should be understood, however, that neither the briefly synopsized summary nor particular definitions hereinabove are not to limit interpretation of the invention to the specific forms and examples but rather on the contrary are to cover all modifications, equivalents and alternatives falling within the scope of the invention.

DESCRIPTION OF THE DRAWINGS

The present invention will be understood and appreciated more comprehensively from the following detailed description taken in conjunction with the appended drawings in which.

Figure 1A:
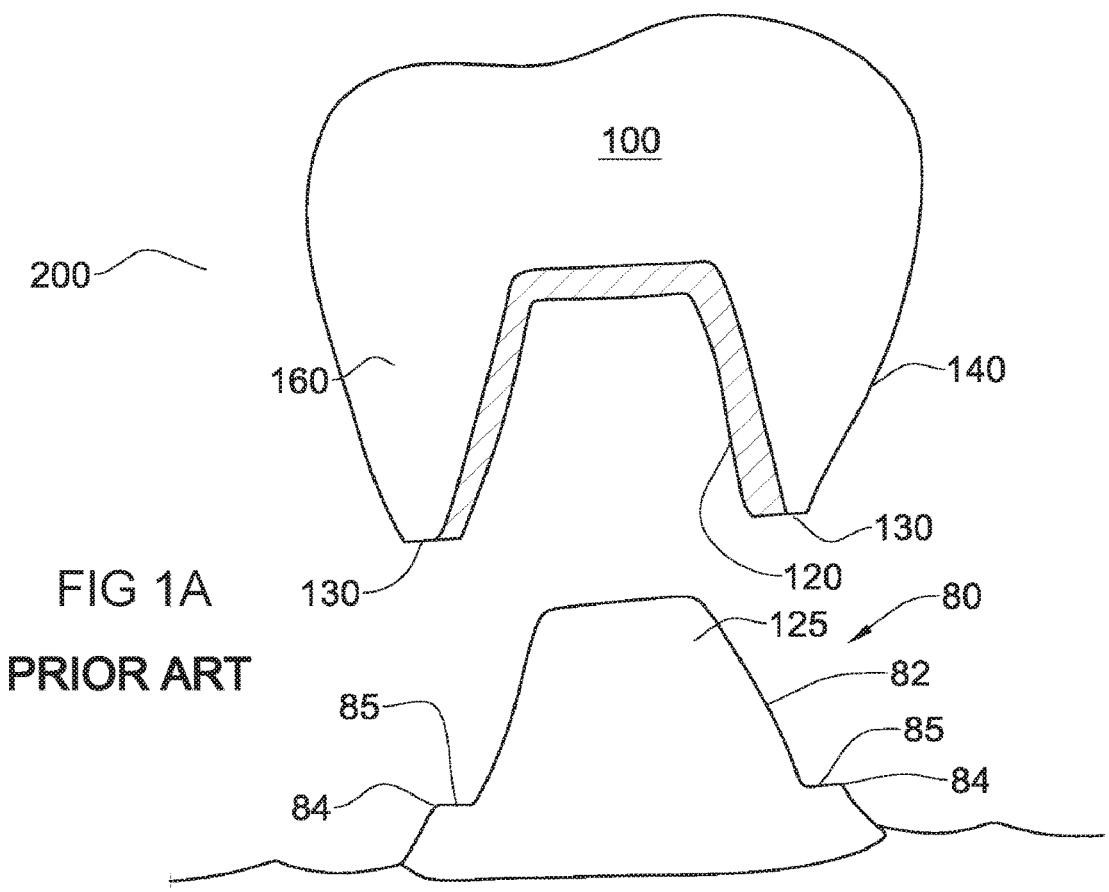
FIG. 1A is an illustration of a prior art virtual crown prosthesis with respect to a virtual preparation area, known from FIG. 4 of US20110070554.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DISCLOSURE OF EMBODIMENTS

Figure 1B:
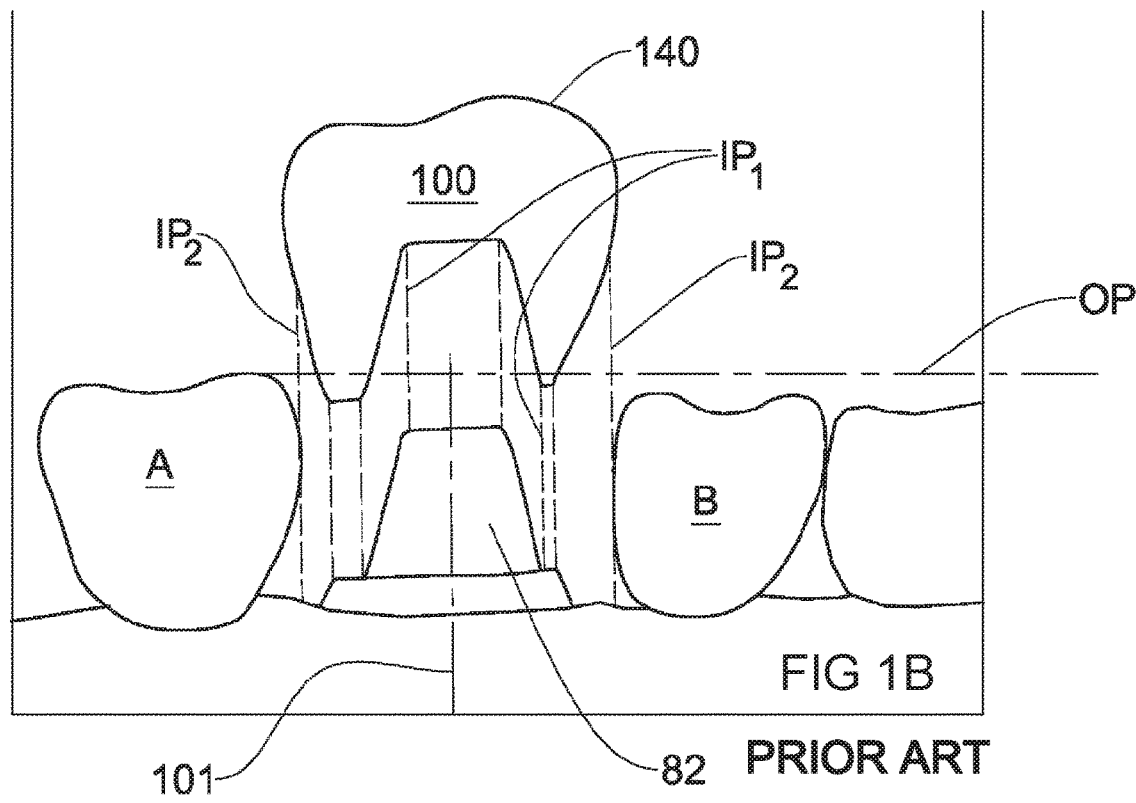
FIG. 1B is an illustration of a prior art insertion path for a crown prosthesis with respect to a preparation, known from FIG. 6 of US20110070554.
Figure 4:
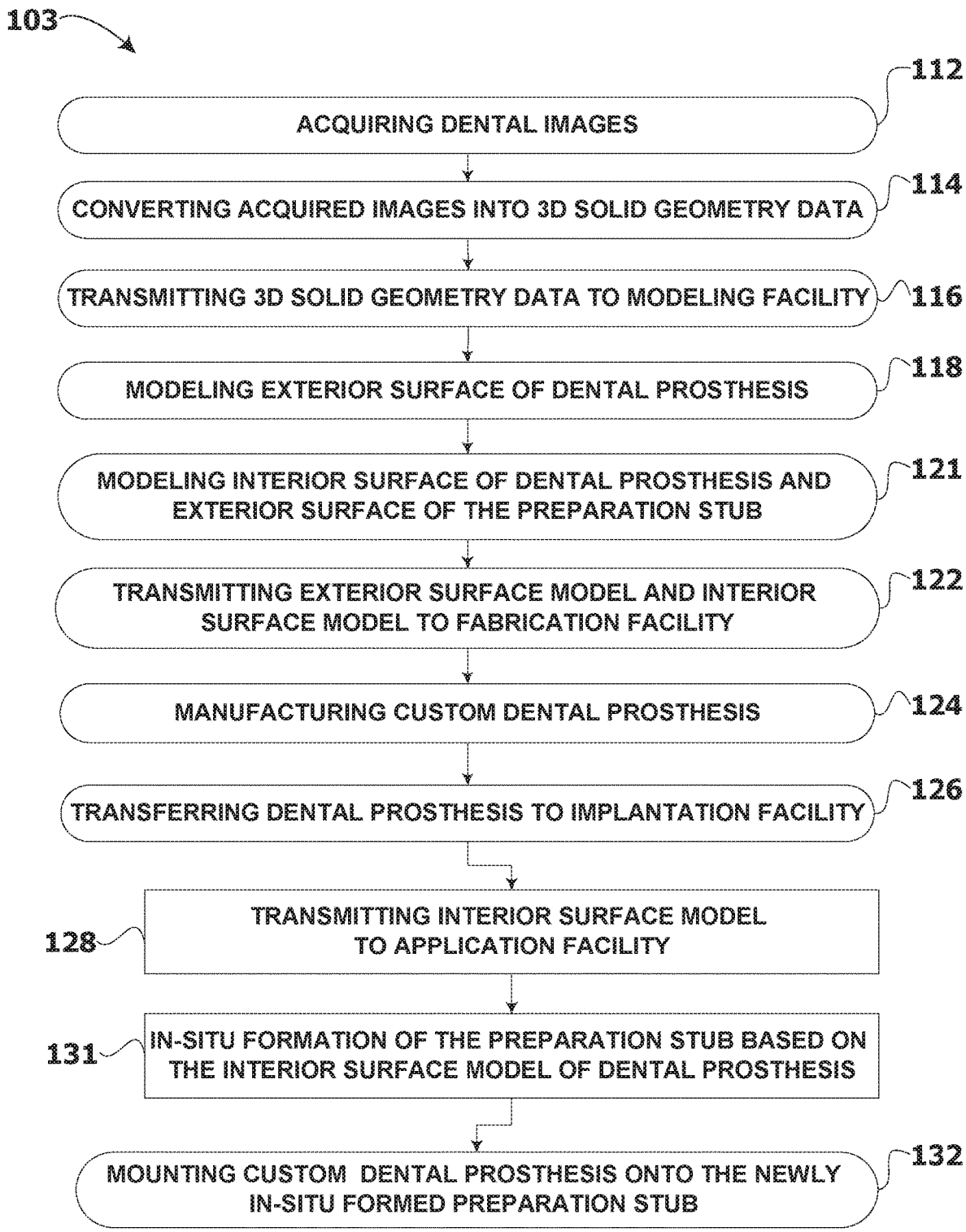
FIG. 4 is a schematic flowchart of an embodiment of the method for automated in-situ preparation for mounting of prefabricated custom dental prosthesis
Figure 6:
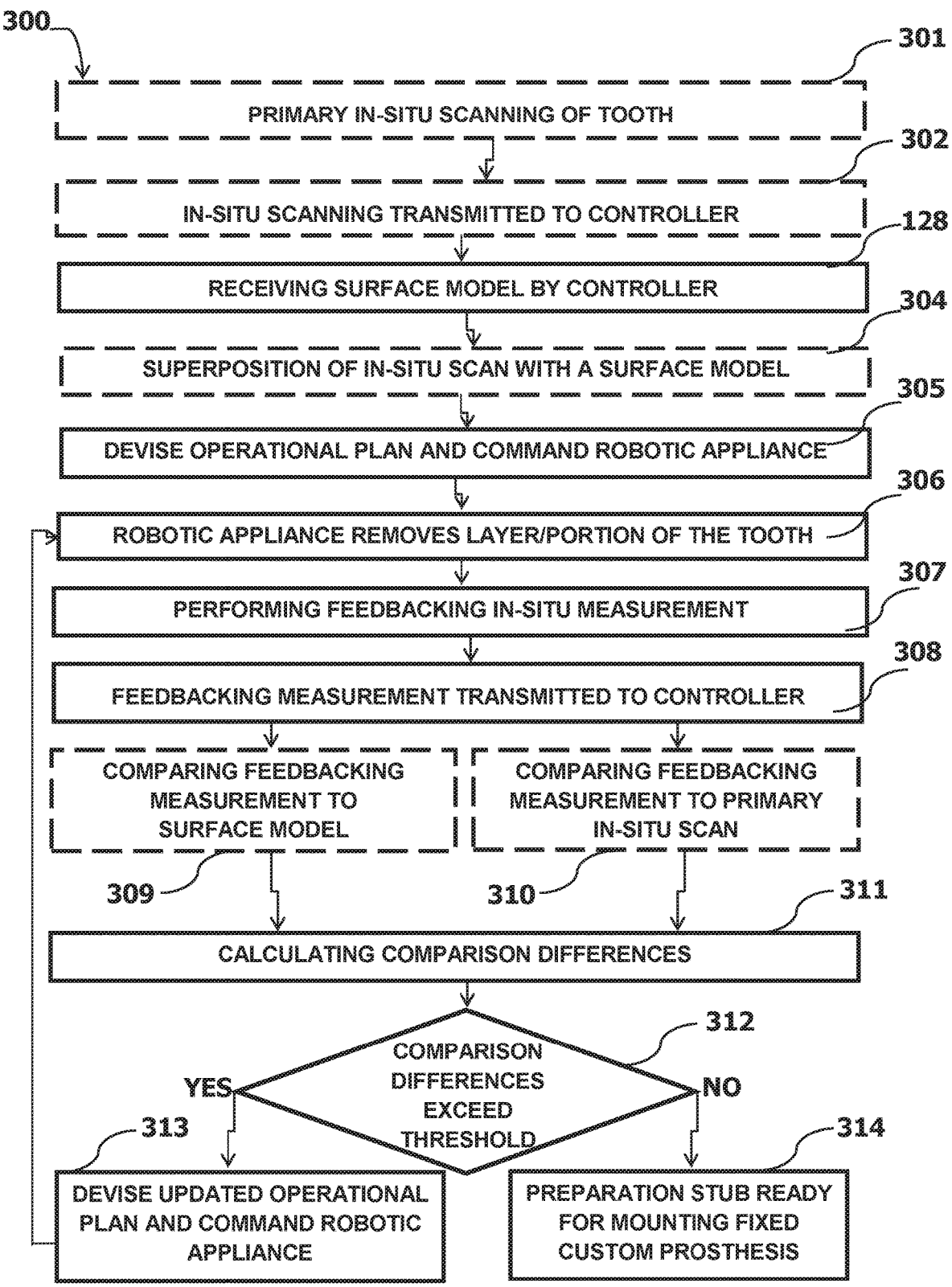
FIG. 6 is a schematic flowchart of an embodiment of a method for controlled automated in-situ preparation utilizing in-situ feedbacking measurements.

Prior to elaborating any embodiment of the present invention, in order to present the background for the inventive concept more clearly, reference is firstly made to FIGS. 1A and 1B, showing prior art virtual crown prosthesis and path for a crown prosthesis with respect to a virtual preparation area, known from FIGS. 4 and 6 of US20110070554.

Referring to FIGS. 1A and 1B, a virtual representation of a crown, generally designated 100, has an internal surface 120 and lower edge 130 that needs to be precisely defined and manufactured to match the preparation 80 and finish line 84, respectively, in the intraoral cavity 200 of a patient. If the crown 100 is to comprise a coping 160, the said internal surface 120 is that of the coping 160. The crown 100, which may be formed from a plurality of layers, preferably needs to have a natural looking appearance. Further, the dimensions of the crown 100, in particular the definition of the external surface 140 depends on external factors and needs to be such as to enable the crown 100 to fit between the adjacent teeth A, B, and to provide proper occlusion with the teeth of the facing jaw.

The external surface 140 of the crown in US20110070554 is such as to provide certain critical linear dimensions that comply with at least one of the target width or target height of a site or location on the jaw on which the crown is to be fitted. The target width may include the mesiodistal size of a tooth that is being replaced by the n 100, and may be defined such as to provide adequate clearance between the crown 100 and adjacent teeth A, B, when the crown 100 is fixed onto the corresponding preparation in the intraoral cavity. The target height of the crown 100 may be defined such as to provide adequate occlusion with the "working side" of the tooth and avoiding interfering contact between the crown and teeth of the opposite jaw when the crown is fixed onto the corresponding preparation 80 in the intraoral cavity.

An outer shape for the external surface 140 in US20110070554 may be chosen in a number of ways. For example, if the original tooth that the crown 100 is replacing is still available, and the outer surface thereof is of a reasonable form, this original tooth may be scanned and the 3D data of the surface obtained. If necessary, this 3D data may be considered as a starting point, and the final shape of the external surface 140 is obtained by manipulating this data as required by the technician or other user that is designing the surface 140. Alternatively, if the patient has a reasonably healthy tooth on the same jaw but on the adjacent quadrant at a position corresponding to where the crown is to be fitted, the 3D data of the surface of this tooth is obtained. Optionally, this tooth may be scanned as described herein to obtain the 3D spatial coordinates thereof, unless this data may already be available from the 3D data of the oral cavity 200 stored in the processor. Typically, such 3D-data would need to be transformed to provide a lateral inversion of the coordinates, suitable for a prosthesis in the other half of the jaw. Alternatively, a suitable profile for surface 140 may be chosen and obtained from a library that comprises the 3D spatial profiles of shapes or profiles of the outer surfaces of a plurality of crowns and teeth. If necessary, the relative size and shape of the surface 140 may be adjusted by the user to better match the other teeth in the jaw. Then, the chosen surface is adjusted in any suitable manner, either manually, automatically, interactively or in any other manner, in order that the required target dimensions of surface 140 will fit within a control volume that defines the maximum dimensions of the crown 100, as required to conform to the space available in the intra oral cavity 200. In particular, the control volume may be chosen such as to provide adequate clearance between the crown and adjacent teeth, and adequate occlusion with the opposite teeth, when the crown 100 is properly fixed onto the preparation.

The suitable software in US20110070554 is used to define the inner surface 120 according to predetermined parameters. These parameters consider the geometries of the external surface of the preparation 80 including finish line 84, the spacing required between the coping (if one is to be used with the crown) or the internal surface of the crown (if no coping is used) and the preparation to accommodate the adhesive or cement that is used to provide the bond between the two. The suitable software in US20110070554 is to provide the external shape of such a coping 160, and thus provide a complete geometrical representation or 3D data of the coping 160, digitally. The external surface of the coping 160 may be defined in any number of ways. Typically, at least a majority of the external surface of the stump 82 is displaced from the internal surface thereof by a uniform amount to provide an approximately constant thickness throughout. However, the thickness of the coping 160 may vary for a number of reasons. For example, it may be necessary in some cases to provide a coping that is stronger in some parts than in others, reflecting the activity that the crown 100 will be expected to engage in as a molar, incisor, canine and so on.

The design of the external surface 140 and the internal surface 120 in US20110070554 may be executed by a processor at the dental clinic, or alternatively at the service center, or at the dental lab. The method of US20110070554 is adapted for providing feedback data regarding the definition of the finish line 84. In particular, it is desired to receive such feedback data referring to the quality and clearness of the finish line 84, and optionally including the shoulder 85. The finish line 84 may be of any type thereof, for example knife edge, feather edge, chamfer, chamfer bevel, shoulder, shoulder bevel, and so on. Alternatively, the finish line 84 may comprise a combination of different types around the periphery of the preparation, for example part of the finish line for a particular preparation may be knife edge, while another part may be feather edge.

Having scanned the intraoral cavity 200, in particular the target zone T including the preparation 80, finish line 84 and (where appropriate) shoulder 85, the processor then manipulates the resulting numerical entity W to identify the finish line 84. This may be done using any suitable algorithm. For this purpose, it may be advantageous for the entity W to also include color components for each surface point defined therein. The differentiation of dental surface color between the hard tissues and the soft tissues may be helpful in automatically defining the finish line, as described in the aforesaid co-pending application entitled "METHOD FOR PROVIDING DATA ASSOCIATED WITH THE INTRAORAL CAVITY". Generally, the shoulder type (e.g., porcelain shoulder, metal collar and so on) should match and be suitable for the prosthesis it is desired to implant at the dental site.

The geometry of the finish line 84 and optionally shoulder 85 in US20110070554 may then be analyzed according to predetermined rules, to establish the relationship between the virtual finish line thus identified, and the function which the finish line 84 and optionally shoulder 85 is to play in the mounting of the prosthesis to the preparation. Such rules may comprise, for example one or more of the following: (a) the finish line is continuous about the full periphery of the preparation; (b) the thickness of the shoulder 85, i.e., the radial dimension between the edge of the finish line 84 and the preparation 80, lies within a predetermined range; (c) the thickness of the shoulder 85 is substantially uniform along the periphery thereof; (d) there are no abrupt changes in slope of the finish line 84 along the periphery thereof; (e) the type of prosthesis to be implanted.

It may then be established in US20110070554 whether the finish line 84 and/or shoulder 85 comply with such rules and can then provide feedback data to the user. Such feedback data may take many different forms. For example, in the positive, i.e., that the finish line, for example, is adequate, the processor may be adapted to transmit a signal via a display. In the negative, i.e., in cases where the finish line is not suitable according to the aforesaid rules, for example, the feedback data may first advise where the finish line is deficient. For example, if referring to the first rule listed above, there is a step or discontinuity along the periphery of the finish line, the location and extent of the same may be alerted to the user. For this purpose, a 3D representation of the preparation site may be displayed, with the part of the finish line in question highlighted in a different color to the rest of the finish line and/or of the preparation and so on. Similarly, if the practitioner is attempting to create a feather edge finish line, deviations in geometry from this type of finish line, for example, part of the finish line is chamfered, may also be alerted to the user, for example by suitably annotating a graphical image of the preparation with colors and so on.

This also enables the practitioner to check whether the finish line is of the type he/she wants, or at least how close it is to this ideal. Further, the feedback data may also comprise indications to the user as to where to modify the finish line 84 or shoulder 85 to achieve better results. In this context, an image of the numerical entity may be displayed in the display, with the finish line 84 and optionally also the shoulder 85 highlighted thereon. Then, the zones of the finish line that require further work may be contrasted with respect to the finish line 84 and/or the shoulder 85, for example by coloring such zones in a different color to the rest of the image. Optionally, zones may be colored differently according to the type of work required. For example, zones deficient with respect to rule (a) above may be colored in red, while those deficient with respect to rule (b) are colored in blue, and so on.

Thus, suggested changes in US20110070554 to the finish line may be displayed on a two-dimensional representation of said dental preparation, via a display, wherein said new finish line geometry may be superimposed over said representation. Modification of the finish line 84 and/or shoulder 85 typically requires a material removing operation, and after doing so, the intra oral cavity 200 may be re-scanned to provide a second numerical entity. The second numerical entity, in particular the portions thereof relating to the finish line 84 or shoulder 85, may then be analyzed as before to determine whether the finish line 84 or shoulder 85 are acceptable according to the predetermined rules, and without reference to the original entity W. Alternatively, the second numerical entity may be compared with the original entity W, and any deviations between the two entities may be highlighted in a display in order to facilitate the next cycle of modification to the finish line.

Alternatively, the processor in US20110070554 may simply display the numerical entity and the highlighted finish line 84 and/or shoulder 85 on a display, and this may at times represent sufficient feedback data for enabling the user to inspect the image thus created and to determine in a subjective manner whether the finish line and/or the shoulder are suitable or not. In all cases, the processor is suitably programmed to enable the numerical entities to be viewed at any suitable angle and/or magnification.

The numerical entity W in US20110070554 may be transmitted to one or more remote locations, such as for example a service center of a dental lab, to be analyzed there by a computer (not shown), or by a skilled technician or another user. The computer or skilled technician at the dental lab may then communicate the results of the analysis to the original user via the communication network, or a different communication network, for example via cellular phone. These results may be in the form of numerical information that may be displayed, for example, or verbal instructions on how to proceed.

The method of US20110070554 is adapted for providing feedback data regarding the suitability of the preparation to accept a prosthesis of a predetermined type. Alternatively, the method according to US20110070554 is adapted for providing feedback data regarding the type of prosthesis that may be suitable for use with the preparation 80. In particular, it is desired to receive such feedback data referring to at least one predetermined dimension, such as for example a characteristic thickness of a prosthesis with respect to the geometry of the preparation and the adjacent teeth A and B.

Having scanned the intraoral cavity 200, per US20110070554 in particular the target zone including the preparation 80 and adjacent teeth A and B, as described above, mutatis mutandis, the processor 52 then manipulates the resulting numerical entity W to identify the external surface 125 of the stump 82 of preparation 80. This may be done, for example, by first identifying the finish line and optionally shoulder, for example as described above, and then isolating the coping surface enclosed by the perimeter defined by the finish line and/or shoulder. Then, an external crown surface 140 is chosen or designed for the crown, such as to fit properly in the space between the adjacent teeth A, B, as described hereinbefore. Then the relationship between the external surface 125 (which is typically closely correlated to the internal surface 120 of the crown 100) or of the internal surface 120, and the external surface 140 may then be analyzed by the processor according to predetermined rules. This serves to establish the relationship between the thickness of the walls of crown 100, and the material from which the real crown (based on such a virtual crown 100) is to be produced as a function of the external surface 140 of the stump. Typically, such a relationship is dependent on the material from which the real crown is to be made.

Referring to FIG. 1B, the geometry of the preparation 82 approximates a right frusto-conical cone, and the central axis 101 thereof is more or less perpendicular to the occlusal plane OP. In this example, the insertion path $IP_1$ of the internal surface constrains the external surface 140 to path $IP_2$, which enables the external surface of the virtual crown 100 to be guided to the mounted position on the preparation without interfering or colliding with other parts of the dentition.

Illustrative embodiments of the invention are described below. In the interest of clarity, not all features of actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

Figure 2A:
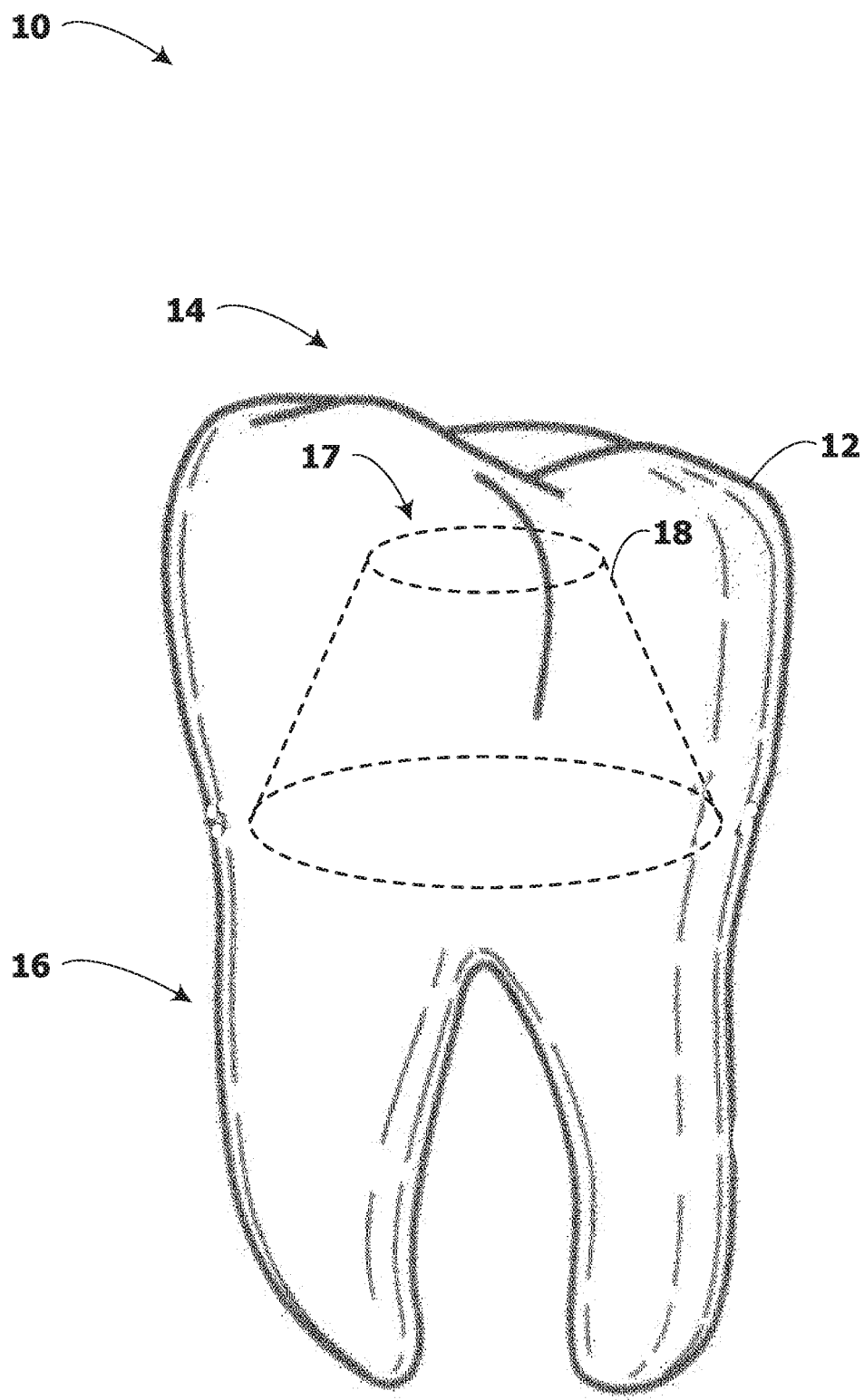
FIG. 2A is an illustration of a tooth subject to future mounting of a fixed dental prosthesis (not shown) thereon, showing a schematic representation of a preparation stub to be formed therein.

In accordance with some embodiments of the present invention, reference is now made to FIG. 2A, showing a schematic illustration of exemplary molar tooth 10, which is subject to future mounting of a fixed dental prosthesis (not shown) thereon. A schematic representation of the geometry of preparation stub 17 defined by exterior surface 18, to be formed of the tissue of tooth 10 is also shown in FIG. 2A. Exemplary tooth 10 embodies coronal portion 14 and apical portion 16 and comprises exterior surface 12.

Figure 2B:
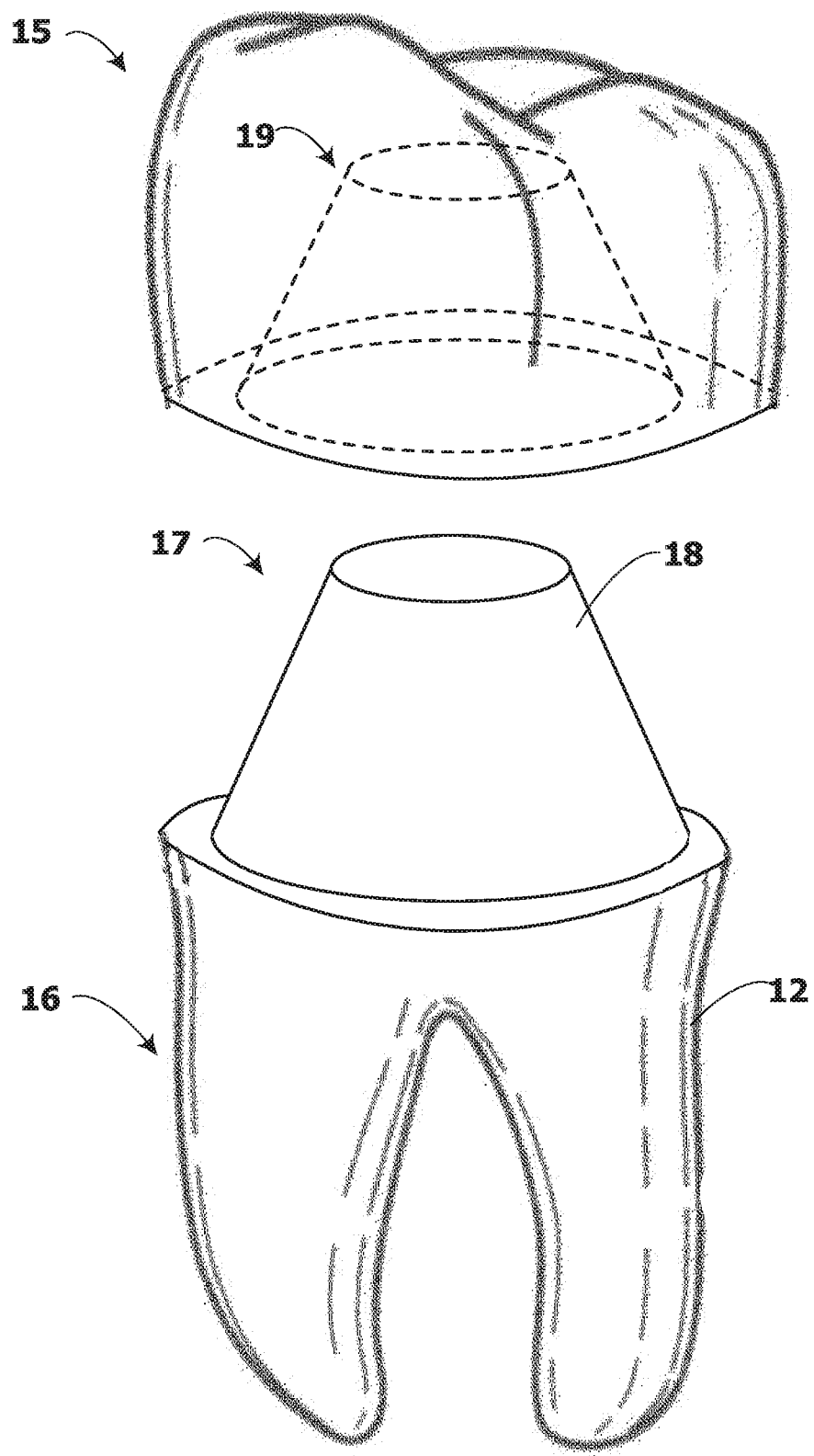
FIG. 2B is a schematic illustration of a prepared tooth, in which the coronal portion of the tooth is prepared for a preparation stub as well as of a dental prosthesis, showing a schematic representation of a respective cavity for the preparation stub therein.

In accordance with some embodiments of the present invention, reference is now made to FIG. 2B, showing apical portion 16 with preparation stub 17 formed thereon. Preparation stub 17 defined by exterior surface 18 is formed by removing dental tissue from a coronal portion of a tooth, such as coronal portion 14 of exemplary molar tooth 10 shown in FIG. 2A. Fixed dental prosthesis 15 to be mounted onto preparation stub 17 comprises recess 19. Recess 19 embodies solid geometry respectively matching exterior surface 18 of preparation stub 17, so that a relatively minor interstice, preferably not exceeding 100 microns, is formed in-between the former and the latter.

Figure 3:
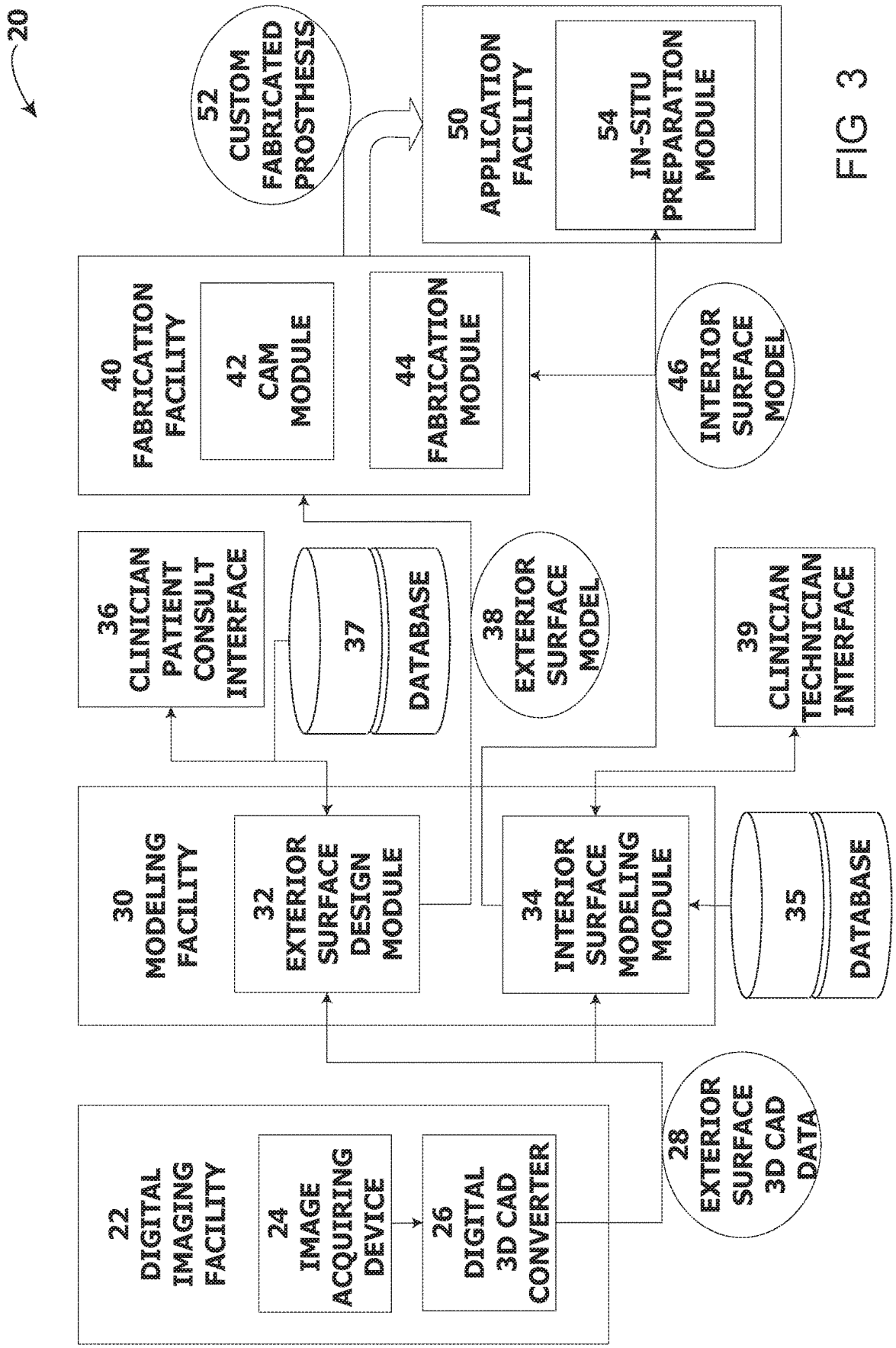
FIG. 3 is a schematic block diagram of an embodiment of the system for automated in-situ preparation for mounting of prefabricated custom dental prosthesis.

In accordance with some embodiments of the present invention, reference is now made to FIG. 3, showing a schematic block diagram of system 20, for automated in-situ preparation for mounting of prefabricated custom dental prosthesis, as well as to FIG. 4, showing a schematic flowchart of an embodiment of method 103 for automated in-situ preparation for mounting of prefabricated custom dental prosthesis. System 20 comprises a digital imaging facility 22. Digital imaging facility 22 of system 20 comprises image acquiring device 24 configured to obtain a plurality of images of patient teeth, which are subject to future dental prosthesis mounting thereon, at step 112. Image acquiring device 24 exemplarily embodies a three-dimensional (3D) scanner, such as optical three-dimensional (3D) scanner, physical touch-based 3D (typically CNC) mapping, x-ray imaging device, a computerized tomography (CT) device, magnetic resonance imaging (MRI) or any other modality configured to obtain a plurality of images of patient teeth, suitable for digitization into three-dimensional solid geometry data, as elaborated hereunder, as well as any combination thereof. It should be that any image acquiring device configured to obtain a plurality of images of patient teeth, employing electromagnetic radiation waves, such as based upon absorption, emission, reflection or scattering, are equally contemplated for those skilled in the art by the current disclosure.

Digital imaging facility 22 of system 20 comprises digital three-dimensional CAD converter 26 configured to process the plurality of images of patient teeth obtained by image acquiring device 24, so as to generate three-dimensional solid geometry CAD data 28, at step 114, representing the exterior surface of patient tooth, subjected to imaging, at step 112, by image acquiring device 24 of digital imaging facility 22. Digital three-dimensional CAD converter 26 typically embodies a dedicated computer hardware and/or software, exemplarily employing techniques elaborated in U.S. Pat. No. 5,345,490, which is incorporated in its entirety herein by this reference.

In one embodiment the three-dimensional solid geometry CAD data 28, representing the exterior surface of patient tooth, comprises an alternate geometry defined discretely rather than with continuous analytic curves and surfaces but still provides a foundation for geometry-dependent applications, such as automatic mesh generation. Once the discrete solid model is created, the automatic mesh generator uses the model to produce a finite element mesh form of an input file. In some embodiments the automatic mesh generator of digital three-dimensional CAD converter 26 uses two algorithms, depending on whether 2-D or 3-D solid meshes are desired. QUADTREE generates two dimensional meshes on arbitrary slices through the data set, whereas OCTREE generates general three dimensional solid meshes. The resulting finite element meshes can be input to any finite element code with a simple formatting code.

Exemplary digital imaging facility 22 of system 20, including image acquiring device 24 as well as digital three-dimensional CAD converter 26, is the iTero Element Intraoral Scanner, available from Cadent, Inc. 640 Gotham Parkway Carlstadt N.J., 07072-2405 USA, set forth in iTero User Guide referenced herein and enclosed hereto, implementing parallel confocal imaging technology for generating three-dimensional dental CAD data 28.

Upon generating three-dimensional solid geometry CAD data 28, at step 114, by digital three-dimensional CAD converter 26, these CAD data 28 are transmitted from digital imaging facility 22 to modeling facility 30, at step 116, to be processed therein, so as to form three different CAD models: (1) a model for the exterior surface of the dental prosthesis, (2) a model for the interior surface of that dental prosthesis, both models to be used for fabrication of the dental prosthesis, and (3) a model for the surface of the preparation stub, to be used by an appliance for in-situ preparation of the stub for the dental prosthesis to be mounted thereon, as elaborated infra.

Modeling facility 30 comprises exterior surface designing module 32 and interior surface modeling module 34. Exterior surface designing module 32 is configured for designing the exterior surface of the dental prosthesis. Interior surface modeling module 34 comprises a dental prosthesis interior surface designing sub-model configured for designing the interior surface of the dental prosthesis and a preparation stub sub-model configured for designing the model for surface of the preparation stub, to be used by an appliance for in-situ preparation of the stub for the dental prosthesis to be mounted thereon. Both exterior surface designing module 32 as well as interior surface modeling module 34 embody dedicated computer hardware and/or software. Exterior surface designing module 32 preferably comprises clinician/patient consult interface 36, accessible by the patient, clinician, dental technician or any other relevant party, so as to provide an input or feedback utilized to design and/or model the exterior surface of the future dental prosthesis. Clinician/patient consult interface 36 is preferably accessible by a clinician/dentist and/or dental technician and/or patient, so that clinical/aesthetic/technical preferences dictated by the clinician/dentist and/or dental technician as well as aesthetic preferences of the patient are effectively addressed in an integrated manner. Exterior surface designing module 32 preferably comprises database 37 containing a plurality of exterior surface dental prosthesis models, representing a common solid geometry of typical human teeth.

Examples of clinician/patient consult interface 36 and/or exterior surface tooth models database 37 and/or designing module 32 in a non-limiting manner include EXOCAD® software available from Exocad GmbH, Julius-Reiber 37 Darmstadt 64293 Germany and set forth in more details at EXOCAD® Partial Framework CAD Technology Preview—Quickstart Guide, referenced herein and annexed hereto. EXOCAD® software provides a state-of-the-art framework with design capabilities of full contour modeling of functional dental prosthesis. It should be acknowledged however that the embodiments of clinician/patient consult interface 36 and/or exterior surface dental prosthesis models database 37 and/or designing module 32 are not limited to EXOCAD® software, whereas numerous other technologies are available for modeling the exterior surface of the dental prosthesis.

The distinct dental prosthesis interior surface designing sub-model and preparation stub sub-model of interior surface modeling module 34 are configured for separately designing the interior surface of the dental prosthesis which is different than the surface of a preparation stub. In some examples the solid geometry of the interior surface of the future dental prosthesis is initially inverted to define a preform of the solid geometry of the surface of the preparation stub and then a tolerance for an interstice, typically not exceeding 100 microns and preferably not exceeding 50 microns, configured to accommodate the adhesive, is deducted across the surface of the preform, to form the solid geometry model of the surface of the preparation stub. In other examples the solid geometry of the surface of the preparation stub and/or the solid geometry of the interior surface of the future dental prosthesis embody complex geometry, more complex than the frusta-conical geometry shown in FIGS. 1A and 1B and/or schematic frusto-conical geometry shown in FIGS. 2A and 2B, configured to address particular clinical and/or technical needs. In yet other examples the solid geometry of the surface of the preparation stub and/or the solid geometry of the interior surface of the future dental prosthesis embody a pyramidal and/or frusto-pyramidal shape. In still other examples the tolerance across the surface of the preparation stub is not uniform and/or constant but rather varying according to clinical and technical constrains/needs.

Moreover, in some preferred examples the solid geometry of the surface of the preparation stub and/or the solid geometry of the interior surface of the future dental prosthesis embody non-symmetrical geometry. In other preferred examples, the solid geometry of the surface of the preparation stub and/or the solid geometry of the interior surface of the future dental prosthesis embody a plurality of structural elements and/or pattern of notches and/or protrusions, configured to enlarge the surface area of the surface of the preparation stub and/or the interior surface of the future dental prosthesis. In yet other preferred examples the solid geometry of the surface of the preparation stub and/or the solid geometry of the interior surface of the dental prosthesis embody a plurality of structural elements and/or pattern of notches and/or protrusions, configured to structurally enhance the attachment of adhesive to the surface of the preparation stub and/or the interior surface of the dental prosthesis. In still other preferred examples the solid geometry of the surface of the preparation stub and/or the solid geometry of the interior surface of the dental prosthesis embody an interlocking geometry, configured to structurally engage and/or interlock the surface of the preparation stub to and/or with the interior surface of the dental prosthesis.

Contradistinctively to the teachings of Kolozsvary in WO2012010916 and US2013/0216972, where the solid geometry of the surface of the preparation stub and/or the solid geometry of the interior surface of the dental prosthesis are considered basically the same digital plan, addressing custom tolerancing, enlarging surface area, sustaining enhancement of the adhesive attachment and/or facilitating an interlocking geometry, between the preparation stub and the interior surface of the dental prosthesis, according to various embodiments of the present invention, clearly entails numerous clinical and technical benefits.

Interior surface modeling module 34 preferably comprises clinician/technician consult interface 39, accessible by the clinician/dentist, dental technician or other relevant party, so as to provide an input or feedback utilized to model the interior surface of the future dental prosthesis and/or exterior surface of the preparation stub. Therefore, optionally the modeling of the interior surface of the future dental prosthesis and/or exterior surface of the preparation stub is performed by both the interior surface modeling module 34 and the exterior surface designing module 32 together and interdependently. Interior surface modeling module 34 preferably comprises database 35 containing a plurality of preparation stub models, representing a common solid geometry of typical preparation stubs for human teeth.

Examples of clinician/technician consult interface 39, and/or interior surface models database 37 and/or modeling module 34 in a non-limiting manner include EXOCAD® Model Creator software available from Exocad GmbH, Julius-Reiber 37 Darmstadt 64293 Germany and set forth in more details at Seamless Integration of the EXOCAD® Model Creator with the Stratasys Eden260V 3D Printing System, referenced herein and annexed hereto. EXOCAD® Model Creator software provides a state-of-the-art framework with design capabilities of modeling the interior surface of the future dental prosthesis and/or exterior surface of the preparation stub. It should be acknowledged however that the embodiments of clinician/technician consult interface 39, and/or interior surface models' database 35 and/or modeling module 34 are not limited to EXOCAD® Model Creator software, whereas numerous other technologies are available for modeling the exterior surface of the dental prosthesis.

Upon completion of designing the exterior surface of the future dental prosthesis by exterior surface design module 32, exterior surface model 38 is generated by modeling facility 30, at step 118. Additionally, upon completing the modeling of the exterior surface of the preparation stub and/or the interior surface of the future dental prosthesis by interior surface modeling module 34 interior surface model 46 is generated by modeling facility 30, at step 121. Upon generating exterior surface model 38 of the exterior surface of the future dental prosthesis as well as interior surface model 46 of the exterior surface of the preparation stub and/or the interior surface of the future dental prosthesis, exterior surface model 38 and interior surface model 46 are transmitted from modeling facility 30 to fabrication facility 40, at step 122, in order to fabricate a preferably permanent dental prosthesis therein, as elaborated hereunder.

Additionally, upon generating interior surface model 46 of the future dental prosthesis and/or of the exterior surface model of the preparation stub, interior surface model 46 is transmitted, at step 128, from modeling facility 30 to application facility 50, such as a dental clinic. It is noted that in this specification as well as in claims hereunder the terms interior surface model 46 of the dental prosthesis and the exterior surface model of the preparation stub are optionally used interchangeably. This is because the geometrical models of the interior surface model 46 of the dental prosthesis and of the exterior surface model of the preparation stub are closely interrelated and in some examples are essentially identical. While in some embodiments a dedicated geometrical model is generated for the interior surface model 46 of the dental prosthesis and additional dedicated geometrical mode is generated for the exterior surface model of the preparation stub, in other embodiments merely one general geometrical model is generated for both the interior surface model 46 of the dental prosthesis as well as for the exterior surface model of the preparation stub. In the latter instance to application facility 50 is capable of generating the exterior surface model of the preparation stub based on the interior surface model 46 of the dental prosthesis.

Fabrication facility 40 is typically a dental technician laboratory or workshop. Fabrication facility 40 preferably comprises a dental computer-aided manufacturing (CAM) module 42, such as the dental CAM disclosed in U.S. Pat. No. 8,954,181. Dental CAM module 42 receives an input comprising exterior surface model 38 and interior surface model 46 and further utilizes both models for computer-aided manufacture of custom fabricated dental prosthesis 52, at step 124, or for computer-aided manufacture of an antisense mold (not shown) for subsequent molding of custom fabricated dental prosthesis 52, at step 124.

Fabrication facility 40 preferably further comprises fabrication module 44. Fabrication module 44 is configured to fabricate custom fabricated dental prosthesis 52, at step 114, from the antisense mold manufactured by dental CAM module 42 and/or to cover custom fabricated prosthetic antisense dental prosthesis 52 with a tooth like ceramic substance.

In one embodiment, upon fabrication, at step 124, custom fabricated dental prosthesis 52 is shipped from fabrication facility 40 to application facility 50, at step 126. As previously mentioned, interior surface model 46 of the exterior surface of the preparation stub and/or the interior surface of the dental prosthesis is transmitted from modeling facility 30 to application facility 50, at step 128. Application facility 50, which is typically a dental clinic, comprises in-situ preparation module 54, configured for automated/machine controlled and/or machine guided/assisted and/or machine supervised formation of the preparation stub, such as preparation stub 17 shown in FIG. 2B, during step 131, according to interior surface model 46 of the exterior surface of the preparation stub and/or the interior surface of the dental prosthesis, received in application facility 50, at step 128.

In another embodiment, upon fabrication at step 124, custom fabricated dental prosthesis 52 is scanned within the fabrication facility 40 using a table top dental scanner and transferred to the modeling facility 30 to be processed therein, so as to form a CAD model for the interior surface of the dental prosthesis and/or exterior surface of the preparation stub, for the dental prosthesis to be mounted thereon. Dental table top scanners include in a non-limiting manner DSi 6000 Dental Impression Scanner by Optical Metrology Ltd. of 10 Hartom St., Jerusalem, Israel. Similarly, interior surface model 46 of the exterior surface of the preparation stub and/or the interior surface of the dental prosthesis is transmitted from modeling facility 30 to application facility 50, at step 128.

In one embodiment, in-situ preparation module 54 comprises a robotic appliance for removal of the dental tissue from the tooth which is performed entirely automatically and/or autonomously. Examples of robotic appliances configured for removal of the dental tissue from a tooth, so as to form a preparation stub, in a non-limiting manner include the intraoral device for automated preparation of the teeth with a view to performing partial or peripheral dental reduction also known as preparation as disclosed in US20150182299.

A preferred example of the robotic appliance configured for removal of the dental tissue from a tooth, so as to form a preparation stub, is disclosed by Takafumi Otani at al. in THE JOURNAL OF PROSTHETIC DENTISTRY, in a study published August 2015 on *In vitro evaluation of accuracy and precision of automated robotic tooth preparation system for porcelain laminate veneers*, annexed hereto. The robotic appliance of Takafumi Otani was tested on twenty right maxillary central incisor tooth models with mean natural tooth dimensions and made out of composite resin and epoxy-resin to simulate enamel and underlying dentin, available as "2-Layered Tooth Model" obtained from Nissin Dental Products Inc, were divided into two groups. Ten tooth models were assigned for tooth preparation with dental robotics as an experimental group, and ten tooth models were assigned for tooth preparation with the conventional free-hand method as a control group.

For the experimental group, three indentations were made on the facial surface of the tooth model with 0.9 mm diameter round diamond rotary cutting instrument 801.31.009 FG Medium Round Diamond obtained from Brasseler USA. These indentations were placed at the incisal and middle thirds, with a depth of half of the 0.9 mm diameter round diamond rotary cutting instrument. These in-dentitions were used to calibrate the robotic arm.

Twenty tooth models were digitally scanned with 3-dimensional (3D) laser scanner model number D700L, obtained from 3Shape A/S. Scanned data were exported as a stereolithography (STL) file and the STL file was 3D reconstructed with 3D computer-aided design (CAD) software SolidWorks, obtained from Dassault Systemes SolidWorks Corp. A tooth preparation for a PLV was designed on the 3D-reconstructed image of a tooth model. The facial tooth reduction was designed with a dimension of 0.5 mm at the incisal third, 0.5 mm at the middle third, and 0.3 mm at the cervical third. A shallow chamfer finish line, of 0.3 mm wide, was designed and placed 1 mm above the free gingival margins. The incisal reduction was designed with a dimension of 1.5 mm and a butt joint design. All line angles and corners were designed to be rounded. Designed tooth preparation data were exported to computational software MATLAB, obtained from The MathWorks Inc, and transformed data were exported to programming software WINCAPS III, obtained from Denso Intl America Inc. The robotic arm was controlled with the latter programming software.

Ten model teeth were mounted on a typodont Prosthetic Restoration Jaw Model, obtained from Nissin Dental Products Inc with a screw. The typodont was attached to the custom mounting unit on a table and stabilized. An electric high-speed handpiece Ti-Max Z95L, obtained from NSK, was attached to the robotic arm VM-60B1G (www.denso-robotics.com/products/vm-g-series/spec) obtained from Denso Intl America Inc., with a custom attachment and a 0.9 mm diameter round diamond rotary cutting instrument was attached to the handpiece. The robotic arm was calibrated by fitting the round diamond rotary cutting instrument into each facial indentation. The rotation speed of the diamond rotary cutting instrument was controlled at 25000 rpm and the speed of the robotic arm movement was controlled at 2 mm per second. The teeth were prepared according to the preoperative preparation design under air-water spray cooling.

The same experimental settings as for the robotic tooth preparation were used and the teeth were prepared in a conventional freehand method according to the same preparation design with the same electric handpiece and the same rotational speed. Facial depth grooves of 0.5 mm were placed on the incisal and middle thirds with a depth cutting diamond rotary cutting instrument model 828.31.026 FG Medium Depth Cutting Diamond, available from Brasseler USA and a 0.3 mm facial depth groove was placed on the cervical third with a 0.3 mm depth cutting diamond rotary cutting instrument 828.31.022 FG Medium Depth Cutting Diamond available from Brasseler USA. All of the grooves were connected with a double grit diamond rotary cutting instrument model 6844.31.016 LVS3 available from Brasseler USA. Incisal depth grooves were placed with a 0.5 mm depth cutting diamond rotary cutting instrument and all of the grooves were connected with the same diamond rotary cutting instrument. This procedure was repeated two times to achieve a 1.5-mm incisal reduction and a silicone matrix Panasil Lab Putty obtained from Kettenbach GmbH & Co KG was used to confirm a 1.5 mm incisal reduction. A 0.3 mm wide finish line was placed 1 mm supragingivally with the fine tip of a double grit diamond rotary cutting instrument, and all the line angles on the tooth preparation were rounded. For both the robotic preparation and conventional freehand preparation, the prepared tooth models were detached from the typodont and digitally scanned with a 3D laser scanner D700L available from 3Shape A/S. Scanned data were exported as an STL file, and the STL file was 3D reconstructed with 3D CAD design software. The postoperative scan image was superimposed on the preoperative preparation design image with computational software and the dimensional differences between these two images was measured with the software at 9 points to measure the facial reduction, at 6 points to measure the finish-line width and at 3 points to measure the incisal reduction. To determine the accuracy and precision of the two groups, the difference between the robotic tooth preparation system and the manual freehand tooth preparation from the preoperative preparation design on the 3D image was computed. The accuracy and precision of the 2-tooth preparation methods were summarized from all sites and separately for each tooth surface, namely: facial, finish-line, incisal.

In second embodiments, in-situ preparation module 54 comprises a clinical appliance for physically guiding and/or assisting in the removal of the dental tissue from the tooth which is performed by the clinician/dentist. Examples of a clinical appliance for physically guiding and/or assisting in the removal of the dental tissue from the tooth in a non-limiting manner include any type of non-autonomous robot-assisted surgery appliance suitable for the purpose of in-situ removal of dental tissue from a tooth, for the formation of the preparation stub, such preparation stub 17 shown in FIG. 2B. Examples of a non-autonomous robot-assisted surgery appliance suitable for the purpose of in-situ removal of dental hard tissue in a non-limiting manner comprises an apparatus for placement of dental implants. Yomi® available from Neocis Inc. at 2800 Biscayne Blvd Suite 600, Miami, Fla. 33137 provides dental surgeons with guidance through the use of haptic robotic technology and multisensory feedback to help achieve the right location, angulation and depth to place the implant exactly according to plan.

In third embodiment, in-situ preparation module 54 comprises at least one robotic arm typically connected to a clinical ablation tool. In third embodiment, in-situ preparation module 54 further comprises a stereoscopic vision sub-module (not shown) or any other means capable of determining the three-dimensional position of the ablation tool relatively to the tooth, so as to detect when a deviation from interior surface model 46 of the exterior surface of the preparation stub and/or the interior surface of the dental prosthesis occurs.

In third embodiment, in-situ preparation module 54 typically translates the hand movements of the dentist, into the movement of the at least one non-autonomous robotic arm, which actually exerts the clinical effect. In some preferred variation, the dentist manipulates the robotic arm and/or the clinical ablation tool manually, whereas in-situ preparation module 54 merely moderates the movements affected by the dentist and/or supervises over these movements affected by the dentist. In some examples, if in-situ preparation module 54 detects a deviation from interior face model 46 of the exterior surface of the preparation stub and/or the interior surface of the dental prosthesis, in-situ preparation module 54 preferably performs at least one of: (1) prevents any further movement of the robotic arm and/or deactivates the robotic arm and/or the clinical ablation tool and/or (2) reduces the intensity of action of the clinical ablation tool and/or (3) alerts the dentist, by producing a stimulus, such as visual, audible or tactile stimuli, in order to prevent an excessive removal of the dental tissue, thereby retaining a close match between the exterior surface of the preparation stub and the interior surface of the dental prosthesis.

In other examples, if in-situ preparation module 54 detects any anticipated deviation from interior surface model 46 of the exterior surface of the preparation stub and/or the interior surface of the dental prosthesis, in-situ preparation module 54 preferably performs at least one of: (1) forces deceleration of any further movement of the robotic arm and/or decelerates the clinical ablation tool and/or (2) reduces the intensity of action of the clinical ablation tool and/or (3) alerts the dentist, by producing a softer stimulus than actual deviation from interior surface model 46 of the exterior surface of the preparation stub and/or the interior surface of the dental prosthesis, such stimulus as visual, audible or tactile stimuli, in order to provoke the dentist's acknowledgment of anticipated excessive removal of the dental tissue, thereby retaining a close match between the exterior surface of the preparation stub and the interior surface of the dental prosthesis.

In third embodiment, in-situ preparation module 54 merely observes the hand movements of the dentist and supervises over them, without somehow interfering with the movements and/or without altering intensity of operation of the ablation tool, which actually exerts the clinical effect. In third embodiment, in-situ preparation module 54 comprises a stereoscopic vision sub-module (not shown) or any other means capable of determining the three-dimensional position of the ablation tool relatively to the tooth, so as do detect when a deviation from interior surface model 46 of the exterior surface of the preparation stub and/or the interior surface of the dental prosthesis occurs.

In forth embodiment, in-situ preparation module 54 uses remote manipulator that allows the surgeon to perform the normal movements associated with the surgery whilst the robotic arms carry out those movements using end-effectors and manipulators to perform the actual surgery on the patient. In forth embodiment, in-situ preparation module 54 comprises a tele-manipulator (not shown) to control the robotic arms and its end-effectors while the visual and/or tactile feedbacking or any other means capable of determining the three-dimensional position of the ablation tool relatively to the tooth, so as do detect when a deviation from interior surface model 46 of the exterior surface of the preparation stub and/or the interior surface of the dental prosthesis occurs.

If in-situ preparation module 54 detects that a deviation from interior surface model 46 of the exterior surface of the preparation stub and/or the interior surface of the dental prosthesis, in-situ preparation module 54 preferably either reduces the intensity of action of the clinical ablation tool and/or alerts the dentist, by producing a stimulus, such as visual, audible or tactile stimuli, in order to prevent an excessive removal of the dental tissue, thereby retaining a close match between the exterior surface of the preparation stub and the interior surface of the dental prosthesis.

Upon completing the automated formation of the preparation stub such as preparation stub 17 in FIG. 2B, by in-situ preparation module 54, at step 131, according to interior surface model 46 of the exterior surface of the preparation stub and/or the interior surface of the dental prosthesis, custom fabricated dental prosthesis 52 is ultimately mounted onto the preparation stub and affixed thereon, typically by specialized adhesives, at step 132.

In order to appreciate one of the technological problems underlying a successful implementation of the present invention, reference is now made to the results, conclusions and discussion of Takafumi Otani at al. in *In vitro evaluation of accuracy and precision of automated robotic tooth preparation system for porcelain laminate veneers*, referenced herein and annexed hereto. According to Takafumi, the precision of robotic tooth preparation achieved by the automated robotic appliance, tested on a fixed tooth model based on a preplanned CAD model was suboptimal, whilst the control performed manually by a skillful dentist has occasionally outperformed the precision of the robotic tooth preparation achieved by the automated appliance. It is further emphasized that suboptimal precision of the robotic tooth preparation was achieved by Takafumi on a fixed tooth model, whereas in real clinical procedures precision is expected to be lower yet, due to the spontaneous movements and breathing of the patient, as set forth in more details infra.

Figure 5:
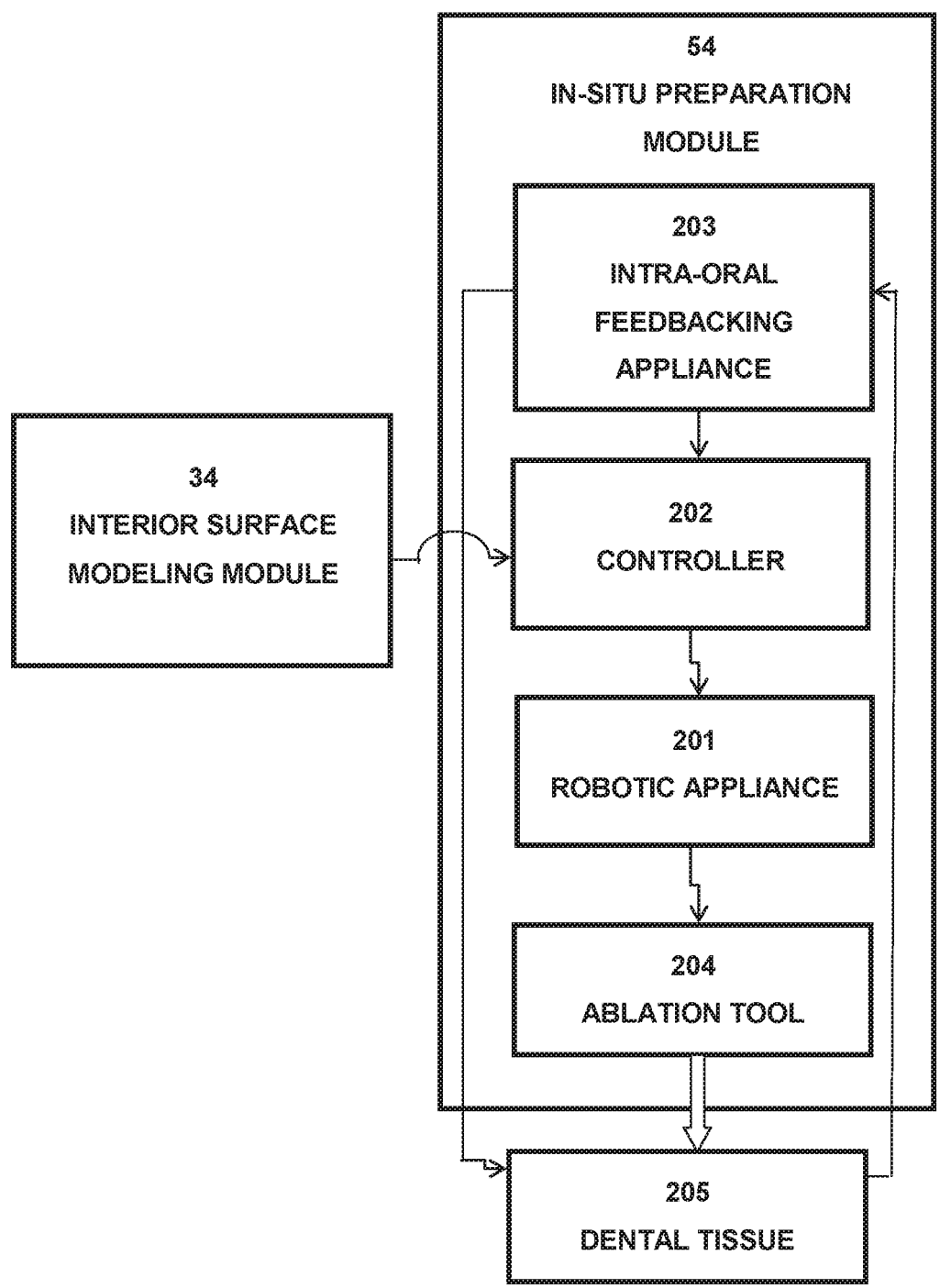
FIG. 5 is a schematic functional block diagram of a preferred embodiment of in-situ preparation module including intra-oral feedbacking appliance.

In accordance with some preferred embodiments of the present invention, enabling a sufficient precision of tolerances not exceeding 100 microns is required. Reference is now made to FIGS. 5 and 6, showing a schematic block diagram of a preferred embodiment of controlled automated in-situ preparation module 54 comprising intra-oral feedbacking appliance 203 as well as a schematic flowchart of a preferred embodiment of method 300 for controlled automated in-situ preparation comprising in-situ feedbacking measurement at step 307, employed by in-situ preparation module 54 of application facility 50.

Controlled automated in-situ preparation module 54, of application facility 50, comprises at least one visual and/or tactile intra-oral feedbacking appliance 203 configured to perform in-situ feedbacking measurement of tooth 10, at step 307. Preferably method 300 of controlled automated in-situ formation of preparation stub 17 commences with primary in-situ scanning of tooth 10, at step 301. Examples of the scanner (not shown) of tooth 10 include the iTero Element Intraoral Scanner, available from Cadent, Inc. 640 Gotham Parkway Carlstadt N.J., 07072-2405 USA and set forth in more details in iTero User Guide, annexed hereto.

The scan obtained during step 301 is then transmitted to the controller 202, at step 302. As previously mentioned, at least interior surface model 46, as well as optionally exterior surface model 38, are transmitted to controller 202 of automated in-situ preparation module 54, at application facility 50, during step 128. Interior surface model 46, as well as preferably exterior surface model 38, received by controller 202 of automated in-situ preparation module 54, at application facility 50, during step 128, is/are then optionally superposed at step 304, with the intra-oral/CT scan obtained during step 301 and received by controller 202, at step 302.

Based on interior surface model 46 and/or exterior surface model 38, received by controller 202 of automated in-situ preparation module 54, during step 128, and/or based on the superposition of interior/exterior surface models 46/38 with the intra-oral scan optionally generated during step 304, an operational plan for robotic appliance 201 is devised by controller 202 at step 305, by calculating inter alia the parameters related to the positioning of the ablation tool, such as the coordinates, vectors and velocities of movements of the ablation tool or acceleration and/or deceleration of the ablation tool, parameters related to actuation of the ablation tool, such as the timing, orientation and position of the activation or response time and movement time, parameters related intensity of operation of the ablation tool, such as the gross power allocated to the ablation tool, maximal rounds per minute (RPM) and/or quota of lumens for the operation of the ablation tool, duration of operational pulses or intervals in-between, as well as optionally various parameters related to operation of optical ablation tools, such as the amplitude, wavelength and/or polarization. Electronic commands are then transmitted from the controller 202 to the robotic appliance 201 and/or ablation tool 204 thereof, so as to remove a primary portion/layer of tooth 10 at step 306.

Subsequently, visual and/or tactile intra-oral feedbacking appliance 203 of automated in-situ preparation module 54, at application facility 50, is actuated to obtain in-situ measurement of the ablation site of tooth 10 at step 307, after and/or during the removal of primary portion/layer of tooth 10 at step 306. The intra-oral feedbacking measurement, obtained during step 307, is then transmitted to the controller 202 at step 308, for subsequent comparison with interior surface/exterior models 46 and/or 38 received by controller 202 of automated in-situ preparation module 54 during step 128, and/or with the primary intra-oral/CT scan obtained during step 301 and received by controller 202 at step 302, as elaborated immediately hereunder. Intra-oral feedbacking appliance 203 of automated in-situ preparation module 54 of application facility 50 comprises a suitable means configured for performing in-situ measurement of the ablation site of tooth 10 at step 307. Examples of an optic means configured for performing in-situ measurement of the ablation site of tooth 10 in a non-limiting manner comprises an apparatus for cutting a workpiece disclosed in U.S. Pat. No. 6,737,607, including a laser beam directed to successive points along the ablation site of tooth 10 surface to be cut and a sensor emitting a sensing beam directed at the same successive points as the cutting beam. A beam combining device receives both the sensor beam and the cutting beam and causes downstream beam segments to be collinear with each other as they impinge tooth 10 surface. In other examples a mechanical means configured for performing in-situ measurement of the ablation site of tooth 10 is implemented, such as a coordinate measuring machine (CMM) employing mechanical contact-probe. In yet another example an optical scanner configured for performing in-situ measurement of the ablation site of tooth 10 is the iTero Element Intraoral Scanner, available from Cadent, Inc. 640 Gotham Parkway Carlstadt N.J., 07072-2405 USA and set forth in more details in iTero User Guide, annexed hereto. In yet another example, an optical scanner configured for performing in-situ measurement of the ablation site of tooth 10 is the iTero Element Intraoral Scanner, available from Cadent, Inc. 640 Gotham Parkway Carlstadt N.J., 07072-2405 USA and set forth in more details in iTero User Guide, annexed hereto.

Upon receiving the intra-oral feedbacking measurement obtained during step 307, by controller 202 at step 308, controller 202 optionally compares, at step 309, the intra-oral feedbacking measurement obtained during step 307 with interior surface/exterior models 46/38 received by controller 202 of automated in-situ preparation module 54 during step 128. Alternatively or additionally, upon receiving the intra-oral feedbacking measurement obtained during step 307, by controller 202 at step 308, controller 202 compares, at step 310, the intra-oral feedbacking measurement obtained during step 307 with the primary intra-oral scan obtained at step 301 and received by controller 202 during step 302.

Upon comparing the intra-oral feedbacking measurement obtained during step 307 with interior surface/exterior models 46/38 received by controller 202 of automated in-situ preparation module 54 during step 128, at step 309, and/or with the primary intra-oral and/or CT scan obtained at step 301 and received by controller 202 during step 302, at step 310, controller 202 calculates the comparison differences between the former and the latter, at step 311.

Controller 202 then determines whether the comparison differences, calculated at step 311, exceed a predetermined safety threshold at step 312, namely whether the amount and/or depth of dental tissue 205 removed exceeds a predetermined safety threshold. The predetermined safety threshold is typically not to exceed 100 microns. Controller 202 then optionally further determines whether the comparison differences, calculated at step 311, do not exceed the predetermined error threshold, at step 312. The predetermined error threshold is dependent upon the accuracy of ablation tool 203 and/or robotic appliance 201. Thus for instance if robotic appliance 201 was commanded by controller 202 to remove 800 micron of dental tissue 205 plus/minus 50 micron, error threshold will be met if robotic appliance 201 has removed between 750 and 850 micron.

If controller 202, determines during step 312 that the comparison differences, calculated at step 311, exceed the predetermined safety threshold, a revised and/or updated operational plan for robotic appliance 201 is advised by controller 202 at step 313. Electronic commands are then transmitted from the controller 202 to robotic appliance 201 and/or ablation tool 204 thereof, so as to remove a primary portion/layer of tooth 10 at iterative step 306. If controller 202, determines during step 312 that the comparison differences, calculated at step 311, exceed the predetermined error threshold a revised and/or updated operational plan for robotic appliance 201 is advised by controller 202 at step 313. Electronic commands are then transmitted from the controller 202 to the robotic appliance 201 and/or ablation tool 204 thereof, so as to remove an additional portion/layer of tooth 10 at iterative step 306. If controller 202, determines during step 312 that the comparison differences, calculated at step 311, do not exceed the predetermined error and safety thresholds, the preparation procedure is optionally concluded, at step 314, and the newly created preparation stub is ready for mounting the fixed dental prosthesis thereon, during step 134, shown in FIG. 4.

In some preferred embodiments, automated in-situ preparation module 54 comprises a means (not shown) configured to mitigate the risk of a spontaneous relative movement of dental tissue 205, such as subject tooth 10 shown in FIG. 2A, relatively to ablation tool 204, which may result from breathing and/or natural movement of the patient, before the completion of step 306. The means for mitigating a relative movement of dental tissue 205, e.g. subject tooth 10 shown in FIG. 2A, relatively to ablation tool 204 in a non-limiting manner comprises mechanical fixation and/or motion capture, as well as any equivalent and/or combination thereof.

In the instance of mechanical fixation, robotic appliance 201 of automated in-situ preparation module 54 comprises a fixator or fastener, configured for attachment to a jaw or any other organ/part of the patient. Accordingly, attachment of the fixator or fastener of robotic appliance 201 to a jaw or other organ/part of the patient renders the spatial coordinate system of ablation tool 204 essentially immovable relatively to the subject tooth, such as tooth 10 shown in FIG. 2A. Therefore breathing and/or natural movement of the patient, before the completion of step 306, essentially does not affect the alignment of ablation tool 204 relatively to the subject tooth. Example of robotic appliance 201 and/or ablation tool 204 and comprising a fixator or fastener, configured for attachment to a jaw by an intraoral splint disposable in the mouth of a patient, including a means for maintaining the position thereof inside the mouth, is disclosed inter alia in US20150182299.

Alternatively or additionally to the mechanical fixation, robotic appliance 201 automated in-situ preparation module 54 comprises a dedicated motion capture device (not shown), operationally connected to controller 202 and/or robotic appliance 201 and/or ablation tool 204, configured for registering the spatial coordinates of a jaw or any other organ/part of the patient, firmly connected to subject tooth, the such as tooth 10 shown in FIG. 2A, as well as continuously tracking the movement and/or position of the subject tooth relatively to robotic appliance 201 and/or ablation tool 204. Example of a dedicated motion capture device (not shown), operationally connected to controller 202, configured for registering the spatial coordinates of a jaw or any other organ/part of the patient, includes the MicronTracker real-time sub-millimeter optical pose-tracking device, available from Claron Technology, at Carlton St 120, Suite 217, Toronto M5A 4K2 Canada and set forth in more details in MicronTracker Developer Manual—ClaroNav, annexed hereto In the instance of a dedicated motion capture device (not shown), method 300 typically further comprises a step (not shown) of attaching tags to a jaw or any other organ/part of the patient, firmly connected to subject tooth; thereby breathing and/or spontaneous movement of the patient, before the completion of step 306, which may affect the alignment of robotic appliance 201 and/or ablation tool 204 relatively to the subject tooth, is/are detectable by the motion capture device (not shown). Upon detecting a spontaneous movement of the patient, before the completion of step 306, which exceeds a predefined safety threshold and is capable to effectively affect the alignment of robotic appliance 201 and/or ablation tool 204 relatively to the subject tooth, such a deviation from the alignment of robotic appliance 201 and/or ablation tool 204 relatively to the subject tooth is communicated to controller 202 and method 300 iteratively performed at least from step 306 onwards.

In the instance of a dedicated motion capture device (not shown), method 300 further comprises a step (not shown) of calibrating the alignment of robotic appliance 201 and/or ablation tool 204 relatively to the subject tooth as well as a step (not shown) of continuously monitoring the initial alignment of robotic appliance 201 and/or ablation tool 204 relatively to the subject tooth. Upon detecting a spontaneous movement of the patient, before the completion of step 306, which exceeds a predefined alignment threshold and is capable to effectively affect the alignment of robotic appliance 201 and/or ablation tool 204 relatively to the subject tooth, method 300 optionally further comprises stopping performing the ablation of step 306 and iteratively performing the aforementioned step (not shown) of aligning robotic appliance 201 and/or ablation tool 204 relatively to the subject tooth.

In some examples automated in-situ preparation module 54 comprising the motion capture device (not shown) embodies a "normally open control" design scheme. However in some preferred examples, automated in-situ preparation module 54 comprising the motion capture device (not shown) embodies a "closed loop control" design scheme with enhanced safety, where the motion capture device (not shown) is operationally connected to controller 202 as well as to the robotic appliance 201 and/or the ablation tool 204. Accordingly to such "closed loop control" scheme, as long as robotic appliance 201 and/or ablation tool 204 receive a signal from the motion capture device (not shown) confirming that robotic appliance 201 and/or ablation tool 204 are sufficiently aligned with subject tooth, the ablation of step 306 proceeds. Once however the signal from the motion capture device (not shown) is interrupted and/or indicates that robotic appliance 201 and/or ablation tool 204 are misaligned relative to the subject tooth, the operation that robotic appliance 201 and/or ablation tool 204 immediately stops.

Figure 7:
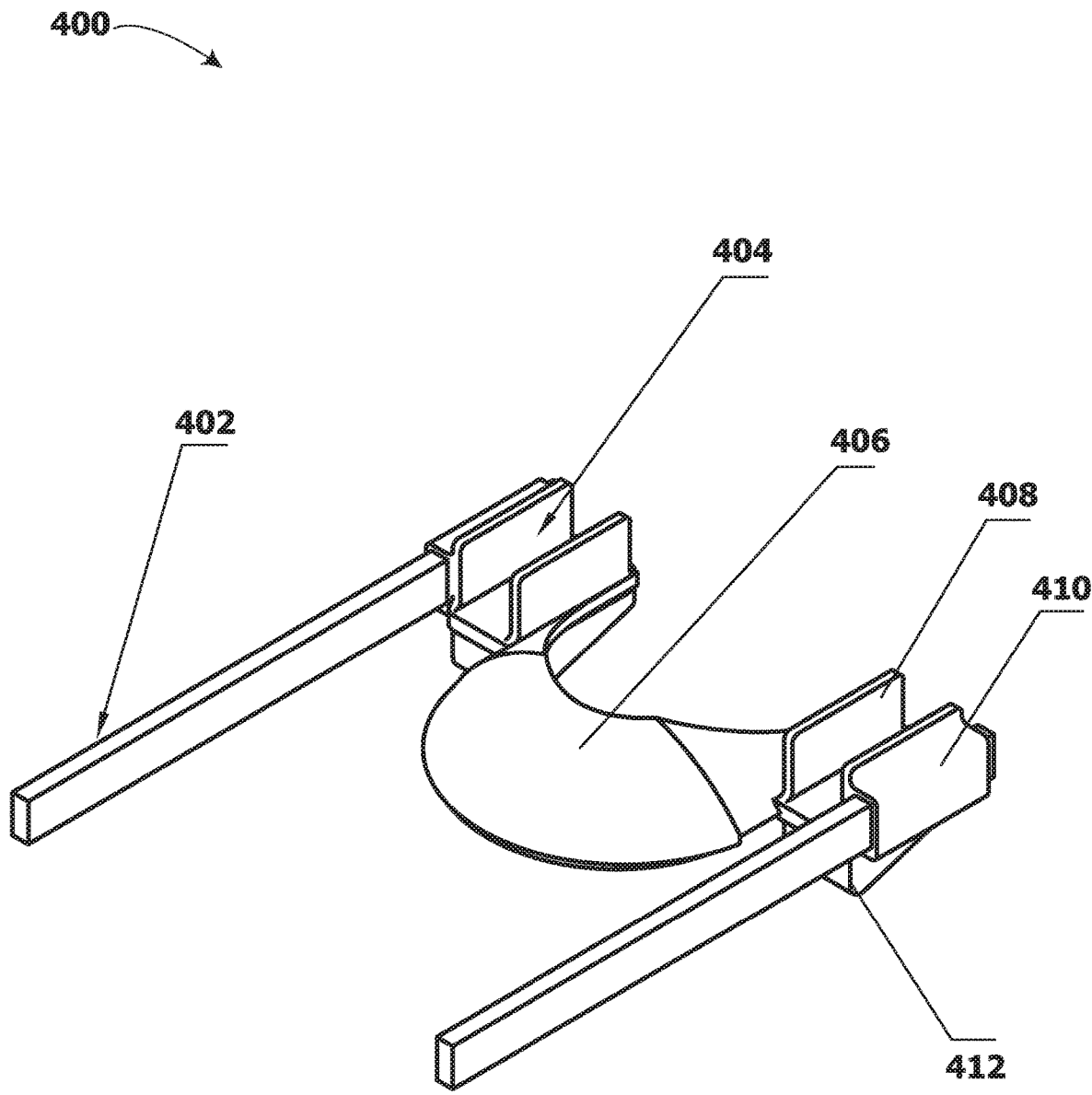
FIGS. 7 to 9 are respectively an isometric, front and top views of an embodiment of a fixation mechanism of in-situ preparation module.
Figure 8:
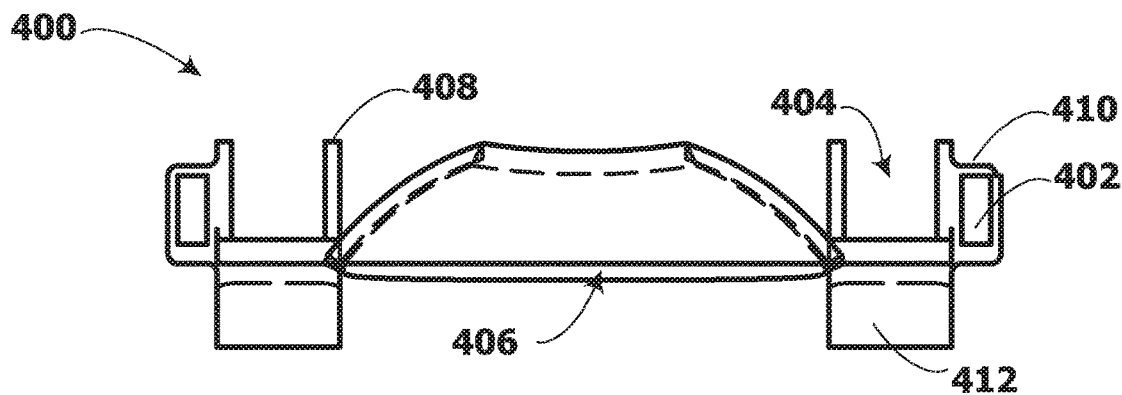
Figure 9:
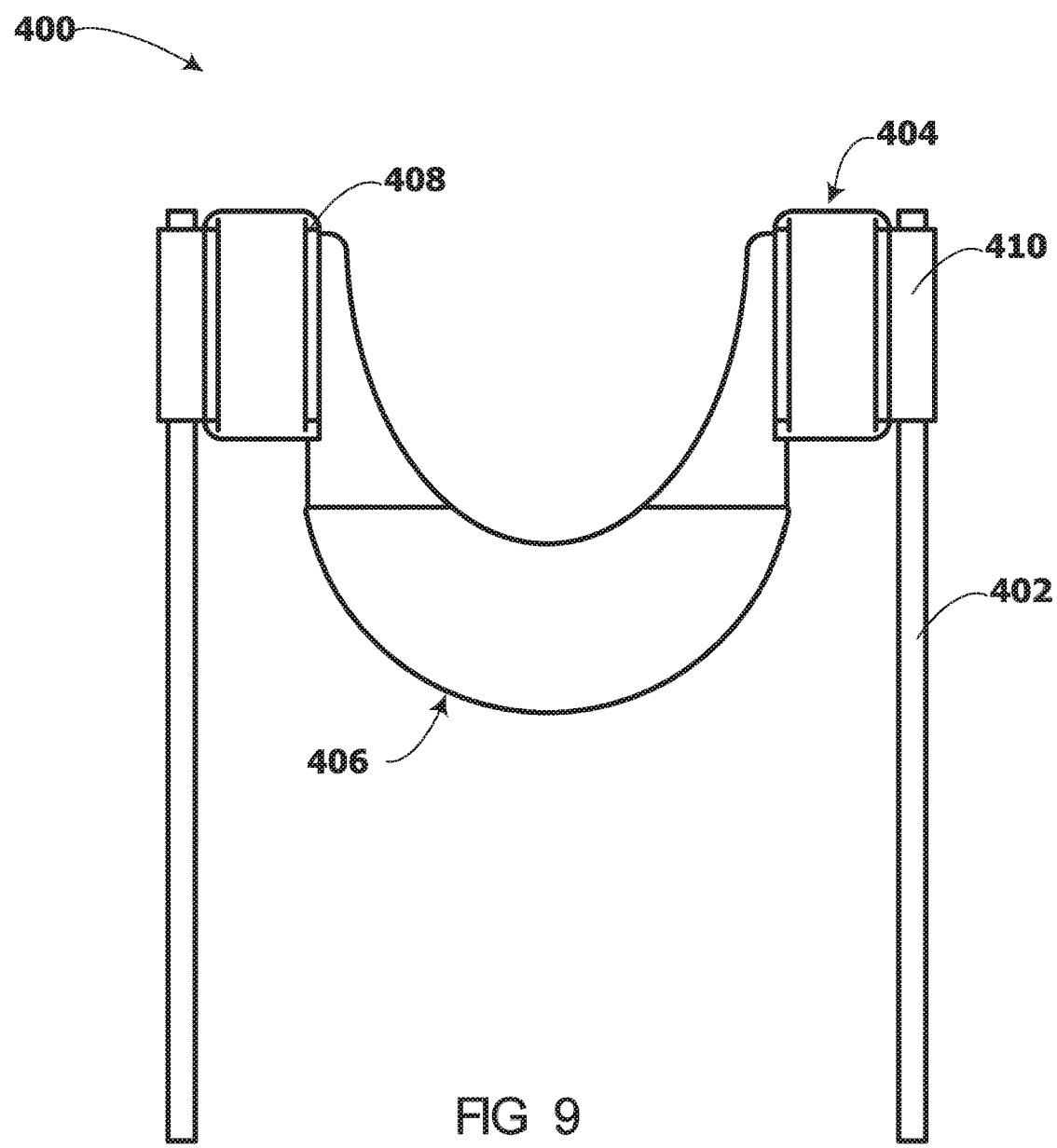

In accordance with some preferred embodiments, reference is now made to FIGS. 7 to 9 respectively showing isometric, front and top views of exemplary fixation mechanism 400 of in-situ preparation module of the present invention. Fixation mechanism 400 comprises molar teeth accommodating portions 404. Molar teeth accommodating portions 404 are confined by ridges 408 from the inner side. Molar teeth accommodating portions 404 are Tillable with a hardening resin (not shown) and configured to affix mechanism 400 to patient's jaw (not shown) by adhering and fastening molar teeth accommodating portions 404 to the molar teeth (not shown) of the patient.

Fixation mechanism 400 further comprises sockets 410, rigidly connectable to molar teeth accommodating portions 404. Sockets 410 are configured for mounting fixation shafts 402, which in turn are rigidly connectable to the in-situ preparation module (not shown) of the present invention.

Fixation mechanism 400 further comprises wedge elements 412, disposed underneath molar teeth accommodating portions 404 and embodying an essentially triangular shape with anteriorly facing pointed end and posteriorly facing thicker end. Wedge elements 412 are typically made of hard elastomeric material. Wedge elements 412 are configured to prevent the patient from closing the jaws while fixation mechanism 400 is installed in patient's mouth.

Fixation mechanism 400 ultimately comprises tongue shielding element 406, extending in-between ridges 408 on the inner side of molar teeth accommodating portions 404. Tongue shielding element 406 is configured to divert patient's tongue away the operational area of the ablating agent of in-situ preparation module.

REFERENCES

US patent application Ser. No. 20150182299 and 20110008751 US patents Ser. No. 5345490, 8954181, 7328077, 6737607 and 7346417 as well as International POT publications No. WO2012010916 and WO2011159503

QUADTREE—Wikipedia, The Free Encyclopedia, 2 Dec. 2015, https://en.wikipedia.org/w/index.php?title=Quadtree OCTREE—Wikipedia, The Free Encyclopedia, 31 Dec. 2015 https://en.wikipedia.org/w/index.php?title=Octree EXOCAD® Partial Framework CAD Technology Preview—Quickstart Guide (Annex 1), available from: Exocad GmbH Julius-Reiber-Str. Darmstadt 37 64293 Germany, retrieved on 27 Feb. 2016 from http://exocad.com/download/techpreview/exocad_Instruction_Manual_Partials_Quickstart_Guide-en.pdf Seamless Integration of the EXOCAD® Model Creator with the Stratasys Eden260V 3D Printing System (Annex 2), available from Stratasys ltd at Holtzman St. Science Park POBox 2496 Rehovot 76124 Israel, retrieved on 29 Feb. 2016 from http://www.stratasys.com/resources/~/media/0C223EB2BD3E498DB4494F6BD0578D8F.pdf THE GLOSSARY OF PROSTHODONTIC TERMS (Annex 3), Volume 94 Number 1

In vitro evaluation of accuracy and precision of automated robotic tooth preparation system for porcelain laminate veneers (Annex 4), by Takafumi Otani at al. in THE JOURNAL OF PROSTHETIC DENTISTRY, published August 2015

The iTero Element Intraoral Scanner User Guide (Annex 5), obtainable from Cadent, Inc. 640 Gotham Parkway Carlstadt N.J., 07072-2405 USA http://www.itero.com/download/iTeroUserGuide.pdf MicronTracker Developer Manual—ClaroNav (Annex 6), obtainable from Claron Technology, at Carlton St 120, Suite 217, Toronto M5A 4K2 Canada, available at: http://www.claronay.com/mt3_brochure.pdf It will be appreciated by persons skilled in the art that the present invention is not limited by what has been particularly shown and described herein above. Rather the scope of the invention is defined by the claims which follow:

The invention claimed is:

1. A system for automated formation of a preparation stub, based on an a priori created computational geometrical model, to conform to a prefabricated fixed dental prosthesis, said system comprises:
   (a) a digital imaging facility, configured to generate a digitized three-dimensional imprint model of at least one subject tooth of a patient, for future mounting of said prefabricated fixed prosthesis thereon, said digital imaging facility comprising:
      (I) an image acquiring device configured to obtain a plurality of images of said subject tooth;
      (II) a three-dimensional data digitizer, operatively connected to said image acquiring device, said three-dimensional data digitizer is configured to receive raw data of said plurality of images of said subject tooth and process said raw data to generate said digitized three-dimensional imprint of said subject tooth;
   (b) a modeling facility operatively connected to said digital imaging facility, configured to receive said digitized three-dimensional imprint model of said subject tooth, said modeling facility comprising:
      (I) a prosthesis exterior surface design module, configured for modelling an exterior surface of said prefabricated prosthesis and generating a digital three-dimensional model of said exterior surface of said prefabricated prosthesis;
      (II) a prosthesis interior surface design module, configured for modelling and generating a respective digital three-dimensional model of an interior surface of said prefabricated prosthesis;
      (III) a stub exterior surface design module, configured for modelling an exterior surface of said preparation stub and generating a digital three-dimensional model of said exterior surface of said preparation stub;
   wherein the exterior surface of said computational geometrical model corresponds to said exterior surface of said preparation stub;
   (c) a fabrication facility operatively connected to said modeling facility and receiving said digital three-dimensional exterior and interior surface models of said prefabricated fixed prosthesis, said fabrication facility comprises at least a computer-aided manufacturing (CAM) module, configured to process a workpiece according to said digital three-dimensional exterior and interior surface models and to manufacture said prefabricated fixed dental prosthesis;
   (d) an application facility operatively connected to said modeling facility and receiving at least one of said digital three-dimensional models of said exterior surface of said preparation stub from said modeling facility, said application facility comprising:
      (I) an ablation tool configured to controllably remove dental tissue from said subject tooth, so as to form said preparation stub;
      (II) an automated in-situ preparation module configured for positioning said ablation tool according to a digital three-dimensional model of said exterior surface of said preparation stub;
   wherein said exterior surface of said preparation stub is different than said interior surface of said prefabricated fixed dental prosthesis;
   (e) a mechanical fixation mechanism comprising:
      (I) molar teeth accommodating portions configured to affix said mechanism to molar teeth;
      (II) fixation shafts rigidly connectable to said molar teeth accommodating portions, said fixation shafts being rigidly connectable to said in-situ preparation module;
      (III) wedge elements disposed underneath said molar teeth accommodating portions and embodying an essentially triangular shape, configured to prevent the jaws from closing while said fixation mechanism is installed;
      (IV) a tongue shielding element, extending in-between said molar teeth accommodating portions, configured to divert a tongue away from an operational area of said ablating tool of said in-situ preparation module.

2. The system, as in claim 1, further comprises an intra-oral feedbacking appliance comprising at least one distance measurement probe, configured to obtain at least one distance measurement of an ablation site on said subject tooth.

3. The system, as in claim 1, further comprises an intra-oral feedbacking appliance, configured to iteratively attain a plurality of distance measurements of an ablation site on said subject tooth and wherein at least one parameter selected from the group consisting of: a parameter related to said positioning of said ablation tool, a parameter related to actuation of said ablation tool and a parameter related intensity of operation of said ablation tool, is repeatedly re-determined according to said a plurality of distance measurements.

4. The system, as in claim 1, wherein said digital imaging facility further comprises a primary in-situ scanner of said image acquiring device, configured to generate said digitized three-dimensional imprint model of said at least one subject tooth.

5. The system, as in claim 1, further comprises a primary in-situ scanner of said image acquiring device and a computational device for superposing a primary in-situ scan comprising said plurality of images of said subject tooth with a digital three-dimensional model of at least one surface selected from the group consisting of: said interior surface of said prefabricated fixed prosthesis and said exterior surface of said preparation stub.

6. The system, as in claim 1, further comprises a primary in-situ scanner of said image acquiring device wherein at least one parameter selected from the group consisting of: a parameter related to said positioning of said ablation tool, a parameter related to actuation of said ablation tool and a parameter related intensity of operation of said ablation tool, is determined with reference to a primary in-situ scan comprising said plurality of images of said subject tooth.

7. The system, as in claim 1, wherein at least one parameter related to said ablation tool, selected from the group consisting of: positional coordinates for said ablation tool, vectors of movements of said ablation tool, velocities of movements of said ablation tool, acceleration and/or deceleration of said ablation tool, response time, movement time, timing of actuation of said ablation tool, orientation of said ablation tool at actuation, position of said ablation tool at actuation, intensity of operation of said ablation tool, gross power allocated to said ablation tool, maximal rounds per minute (RPM), quota of lumens for operation of said ablation tool, duration of operational pulses, duration of intervals in-between said operational pulses, amplitude, wavelength and polarization, is determined with reference to at least one of said digital three-dimensional models.

8. The system, as in claim 1, further comprises a mechanism configured to mitigate a spontaneous relative movement of said subject tooth relative to said ablation tool comprising a dedicated motion capture device.

9. A method of automated formation of a preparation stub, based on an a priori created computational geometrical model, configured to conform to a prefabricated fixed dental prosthesis, said method comprises the steps of:
   (a) obtaining a plurality of images of at least one subject tooth of a patient, for future mounting of said prefabricated fixed prosthesis thereon;
   (b) processing raw data of said plurality of images of said subject tooth and generating a digitized three-dimensional imprint model of said subject tooth;
   (c) transmitting said digitized three-dimensional imprint model of said subject tooth to a modeling facility;
   (d) modeling an exterior surface of said prefabricated prosthesis and generating a digital three-dimensional model of said exterior surface of said prefabricated prosthesis;
   (e) modelling an interior surface of said prefabricated prosthesis and generating a digital three-dimensional model of said interior surface of said prefabricated prosthesis;
   (f) modelling an exterior surface of said preparation stub and generating a digital three-dimensional model of said exterior surface of said stub; wherein the exterior surface of said computational geometrical model corresponds to said exterior surface of said preparation stub;
   (g) processing a workpiece according to said digital three-dimensional exterior and interior surface models of said prefabricated prosthesis to manufacture said prefabricated fixed dental prosthesis;
   (h) transmitting the digital three-dimensional model of said exterior surface of said preparation stub, as an input to a controller of an automated in-situ preparation module;
   (i) devising an operational plan for said automated in-situ preparation module based on said digital three-dimensional model of said exterior surface of said preparation stub;
   (j) commanding said automated in-situ preparation module to controllably remove and/or guide and/or assist controllably removing a portion of dental tissue from said subject tooth according to said operational plan;
   (k) mechanically affixing a fastener of a robotic appliance relative to said subject tooth comprising:
      (I) disposing molar teeth accommodating portions configured to affix said mechanism to molar teeth over molar teeth;
      (II) rigidly connecting fixation shafts of said in-situ preparation module to said molar teeth accommodating portions;
      (III) inserting wedge elements disposed underneath said molar teeth accommodating portions and embodying an essentially triangular shape, configured to prevent the jaws from closing while said fixation mechanism is installed;
      (IV) positioning a tongue shielding element, to extend in-between said molar teeth accommodating portions and divert a tongue away from an operational area.

10. The method as in claim 9, further comprises at least one step selected from the group consisting the steps of:
   (a) performing at least one feedbacking in-situ measurement of an ablation site on said subject tooth;
   (b) comparing results of said at least one feedbacking in-situ measurement of said ablation site on said subject tooth to the digital three-dimensional model of said interior surface of said prefabricated fixed prosthesis and said exterior surface of said preparation stub;
   (c) determining whether differences determined at said step of comparing exceed a predetermined threshold;
   (d) devising an updated operational plan for said automated in-situ preparation module and commanding said automated in-situ preparation module to controllably remove yet another portion of said dental tissue from said subject tooth, if said differences determined at said step of comparing are found to exceed said predetermined threshold at said step of determining.

11. The method, as in claim 10, wherein said predetermined threshold does not exceed 100 microns.

12. The method, as in claim 10, further comprises performing primary in-situ scanning to obtain said plurality of images of said subject tooth; wherein said step of transmitting further comprising transmitting to said controller a primary in-situ scan comprising said plurality of images; wherein said step of devising further comprising devising said operational plan according to said primary in-situ scan comprising said plurality of images; wherein said step of comparing further comprising comparing results of said at least one feedbacking in-situ measurement to said primary in-situ scan comprising said plurality of images, and wherein said step of devising said updated operational plan comprising devising said updated operation plan with reference to said primary in-situ scan comprising said plurality of images.

13. The method, as in claim 9, further comprises iteratively performing a plurality of distance measurements of said ablation site on said subject tooth and repeatedly performing said steps comparing, determining and devising said updated operational plan.

14. The method, as in claim 9, further comprises performing primary in-situ scanning to obtain said plurality of images of said subject tooth.

15. The method, as in claim 9, further comprises performing primary in-situ scanning to obtain said plurality of images of said subject tooth and further superposing a primary in-situ scan comprising said plurality of images with a digital three-dimensional model of at least one surface selected from the group consisting of: said interior surface of said prefabricated fixed prosthesis and said exterior surface of said preparation stub.

16. The method, as in claim 9, wherein said devising comprises calculating at least one parameter selected from the group consisting of: positional coordinates for said ablation tool, vectors of movements of said ablation tool, velocities of movements of said ablation tool, acceleration and/or deceleration of said ablation tool, response time, movement time, timing of actuation of said ablation tool, orientation of said ablation tool at actuation, position of said ablation tool at actuation, intensity of operation of said ablation tool, gross power allocated to said ablation tool, maximal rounds per minute (RPM), quota of lumens for operation of said ablation tool, duration of operational pulses, duration of intervals in-between said operational pulses, amplitude, wavelength and polarization.

17. The method, as in claim 9, further comprises a step selected from the group consisting of: aligning said ablation tool relative to said subject tooth and continuously monitoring movements of said ablation tool relative to said subject tooth.

* * * * *